US007807659B2

(12) United States Patent
Diu-Hercend et al.

(10) Patent No.: US 7,807,659 B2
(45) Date of Patent: *Oct. 5, 2010

(54) CASPASE INHIBITORS AND USES THEREOF

(75) Inventors: Anita Diu-Hercend, Charenton le Pont (FR); Julian Golec, Ashbury (GB); Thierry Hercend, Charenton le Pont (FR); Ronald Knegtel, Abingdon Oxfordshire (GB); Paul Lang, Viuz-en-Sallaz (FR); Andrew Miller, Upton (GB); Karen Miller, West Ilsley (GB); Michael Mortimore, Burford Oxforshire (GB); Peter Weber, Abingdon Oxfordshire (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1056 days.

This patent is subject to a terminal disclaimer.

(21) Appl. No.: 11/522,375

(22) Filed: Sep. 14, 2006

(65) Prior Publication Data
US 2007/0010457 A1 Jan. 11, 2007

Related U.S. Application Data

(63) Continuation of application No. 10/127,324, filed on Apr. 19, 2002, now abandoned.

(60) Provisional application No. 60/285,051, filed on Apr. 19, 2001.

(51) Int. Cl.
*A61K 31/675* (2006.01)
*A01N 57/00* (2006.01)
(52) U.S. Cl. .............................. 514/79; 514/80; 514/85; 514/89; 514/91; 514/92; 514/114
(58) Field of Classification Search ........................ None
See application file for complete search history.

(56) References Cited

U.S. PATENT DOCUMENTS 5,225,528 A   7/1993  Bock et al.
7,410,956 B2 *  8/2008  Mortimore et al. ............ 514/79

FOREIGN PATENT DOCUMENTS

| WO | WO 96/40647 | 12/1996 |
|---|---|---|
| WO | WO 97/22619 | 6/1997 |
| WO | WO 98/11129 | 3/1998 |
| WO | WO 98/16502 | 4/1998 |
| WO | WO 99/18781 | 4/1999 |
| WO | WO 99/47154 | 9/1999 |
| WO | WO 00/23421 | 4/2000 |
| WO | WO 00/61542 | 10/2000 |
| WO | WO 01/44214 | 6/2001 |
| WO | WO 02/22611 A2 | 3/2002 |

OTHER PUBLICATIONS

Dinarello, "Interleukin-18," *Methods*, 19(1):121-132 (1999).
D. Boudard et al., "Expression and Activity of Caspases 1 and 3 in Myelodysplastic Syndromes." Leukemia, 14, 2045-2051 (2000).
Y. Cheng et al., "Caspase Inhibitor Affords Neuroprotection with Delayed Administration in a Rat Model of Neonatal Hypoxic-Ischemic Brain Injury." J. Clin Invest., 101(9), 1992-1999 (1998).
R. E. Dolle et al., "P1 Aspartate-Based Peptide α-((2,6-Dichlorobenzoyl)oxy)methyl Ketones as Potent Time-Dependent Inhibitors of Interleukin-1β-Converting Enzyme." *J. Med. Chem.*, 37(5), 563-564 (1994).
N. Droin et al., "Upregulation of CASP Genes in Human Tumor Cells Undergoing Etopside-Induced Apoptosis." *Oncogene*, 16, 2885-2894 (1998).
R. E. Ellis et al., "Mechanisms and Functions of Cell Death." *Annu. Rev. Cell Biol.*, 7, 663-698 (1991).
M. Endres et al., "Attenuation of Delayed Neuronal Death After Mild Focal Ischemia in Mice by Inhibition of the Caspase Family." *Journal of Cerebral Blood Flow and Metabolism*, 18, 238-247 (1998).
S. Faderl et al., "Caspase 2 and Caspase 3 as Predictors of Complete Remission and Survival in Adults with Acute Lymphoblastic Leukemia." *Clinical Cancer Research*, 5, 4041-4047 (1999).
P. Golstein, "Cell Death in Us and Others." *Science*, 281 (Aug. 28, 1998).
S. R. Grobmyer et al., "Peptidomimetic Fluoromethylketone Rescues Mice from Lethal Endotoxic Shock." *Molecular Medicine*, 5, 585-594 (1999).
T. E. Hedlund et al., "Fas-Mediated Apoptosis in Seven Human Prostate Cancer Cell Lines: Correlation with Tumor Stage." *The Prostate*, 36, 92-101 (1998).
A. Lévesque et al., "Improved Fluorescent Bioassay for the Detection of Tumor Necrosis Factor Activity." *Journal of Immunological Methods*, 178, 71-76 (1995).

(Continued)

*Primary Examiner*—Patrick T Lewis
(74) *Attorney, Agent, or Firm*—Ropes & Gray LLP; James F. Haley, Jr.

(57) ABSTRACT

The present invention relates to novel classes of compounds of formula I which are caspase and TNF-alpha inhibitors. This invention also relates to pharmaceutical compositions comprising these compounds. The compounds and pharmaceutical compositions of this invention are particularly well suited for inhibiting caspase and TNF-alpha activity and consequently, can be advantageously used as agents against caspase-, interleukin-1-("IL-1"), apoptosis-, interferon-γ inducing factor-(IGIF), interferon-γ-("IFN-γ"), or TNF-alpha mediated diseases, including inflammatory diseases, autoimmune diseases, destructive bone disorders, proliferative disorders, infectious diseases, and degenerative diseases. This invention also relates to processes for preparing the compounds of this invention. This invention also relates to methods for inhibiting caspase and TNF-alpha activity and decreasing IGIF production and IFN-γ production and methods for treating caspase-, interleukin-1, apoptosis-, and interferon-γ-, and TNF-alpha mediated diseases using the compounds and compositions of this invention.

12 Claims, No Drawings

OTHER PUBLICATIONS

J. Li et al., "The Mechanism of Apoptosis in Human Platelets During Storage." *Transfusion*, 40, 1320-1329 (2000).

X-S. Liu et al., "The Significance of Changes in Serum Tumour Necrosis Factor (TNF) Activity in Severely Burned Patients." *Burns*, 20(1), 40-44 (1994).

A. M. M. Mjalli et al., "Phenylalkyl Ketones as Potent Reversible Inhibitors of Interleukin-1β Converting Enzyme." *Bioorganic & Medicinal Chemistry Letters*, 3(12), 2689-2692 (1993).

S. Natori et al., "Apoptosis of Sinusoidal Endothelial Cells Occurs During Liver Preservation Injury by a Caspase-Dependent Mechanism." *Transplantation*, 68(1), 89-96 (1999).

D. W. Nicholson et al., "Identification and Inhibition of the ICE/CED-3 Protease Necessary for Mammalian Apoptosis." *Nature*, 376, 37-43 (1995).

N. Özören et al., "The Caspase 9 Inhibitor Z-LEHD-FMK Protects Human Liver Cells While Permitting Death of Cancer Cells Exposed to Tumor Necrosis Factor-related Apoptosis-inducing Ligand." *Cancer Research*, 60, 6259-6265 (2000).

T. A. Rano et al., "A Combinatorial Approach for Determining Protease Specificities: Application to Interleukin-1β Converting Enzyme (ICE)." *Chemistry & Biology*, 4(2), 149-155, (1997).

I. Rodriguez et al., "Systemic Injection of a Tripeptide Inhibits the Intracellular Activation of CPP32-like Proteases In Vivo and Fully Protects Mice Against Fas-mediated Fulminant Liver Destruction and Death." *J. Exp. Med.* 184, 2067-2072, (1996).

Y. Sasaki et al., "Immunohistochemical study of Fas, Fas Ligand and Interleukin-1β Converting Enzyme Expression in Human Prostatic Cancer." *British Journal of Urology*, 81(6), 852-855 (1998).

G. S. Schierle et al., "Caspase Inhibition Reduces Apoptosis and Increases Survival of Nigral Transplants." *Nature Medicine*, 5(1), 97-100 (1999).

N. A. Thornberry, "Caspases: Key Mediators of Apoptosis." *Chemistry & Biology*, 5, R97-R103 (1998).

N. A. Thornberry et al., "Caspases: Enemies Within." *Science*, 281, 1312-1316 (1998).

N. A. Thornberry et al., "Inactivation of Interleukin-1β Converting Enzyme by Peptide (Acyloxy)methyl Ketones." *Biochemistry*, 33, 3934-3940 (1994).

A. G. Yakoviev et al., "Activation of CPP32-like Caspases Contributes to Neuronal Apoptosis and Neurological Dysfunction after Traumatic Brain Injury." *The Journal of Neuroscience*, 17(19), 7415-7424 (1997).

H. Yaoita et al., "Attenuation of Ischemia/Reperfusion Injury in Rats by a Caspase Inhibitor." *Circulation*, 97(3), 276-281 (1998).

W. Vendeville et al., "Indentification of Inhibitors of an 80 kDa Protease from *Typanosoma cruzi* through the Screening of a Combinatorial Peptide Library." *Chem. Pharm. Bull.*, 47(2), 194-198 (1999).

Bock et al., *Chemical Abstract*, vol. 117; 90798, 1998.

"Alzheimer's Disease: Fact Sheet", NIH Publication No. 03-3431 (Sep. 2005), Alzheimer's Disease Education & Referral (ADEAR) Center, A Service of the National Institute on Aging, National Institutes of Health, U.S. Dept. of Health and Human Services.

Delagarza, V. *Clinical Pharmacology* (2003), vol. 68, pp. 1365-1372.

"Dengue Fact Sheet", Jan. 7, 2005, Department of Health and Human Services, Centers for Disease Control and Prevention, pp. 1-3.

Lopalco, L. *Current HIV Research* (2004), vol. 2, pp. 127-139.

\* cited by examiner

CASPASE INHIBITORS AND USES THEREOF

CROSS REFERENCE TO RELATED APPLICATIONS

This application is a continuation of co-pending U.S. patent application Ser. No. 10/127,324, filed Apr. 19, 2002, which in turn claims priority to U.S. Provisional Patent Application 60/285,051, filed Apr. 19, 2001, the content of all of which is incorporated by reference.

FIELD OF THE INVENTION

This invention is in the field of medicinal chemistry and relates to novel compounds, and pharmaceutical compositions thereof, that inhibit caspases and/or TNF-alpha that mediate cell apoptosis and inflammation and inhibit pathophysiologic effects of excessive amounts of TNF-alpha in a mammal. The invention also relates to processes for preparing and methods of using the compounds and pharmaceutical compositions of this invention to treat diseases where caspase and/or TNF-alpha activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science,* 1998, 281, 1283-1312; and Ellis et al., *Ann. Rev. Cell. Biol.,* 1991, 7, 663).

Caspases are a family of cysteine protease enzymes that are key mediators in the signaling pathways for apoptosis and cell disassembly (Thornberry, *Chem. Biol.,* 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognizes aspartyl residues at both positions 1 and 4 on the N-terminal side of the cleavage site, and preferably a sequence of Asp-Glu-X-Asp. A third group, which includes caspases 6, 8, 9 and 10, tolerates many amino acids in the primary recognition sequence, but seems to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector caspases 3, 6 and 7, is involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$—[P4]-[P3]-[P2]—$CH(R)$ $CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); and Nicholson et al., *Nature* 376, 37-43 (1995). Irreversible inhibitors based on the analogous tetrapeptide recognition sequence have been prepared where R is an acyloxymethylketone (—$COCH_2OCOR'$), wherein R' is exemplified by an optionally substituted phenyl such as 2,6-dichlorobenzoyloxy, and where R is $COCH_2X$ wherein X is a leaving group such as F and Cl. Thornberry et al., *Biochemistry* 33, 3934 (1994); and Dolle et al., *J Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to effectively treat fulminant liver destruction, and to improve survival after endotoxic shock. Yaoita et al., *Circulation,* 97, 276 (1998); Endres et al., *J Cerebral Blood Flow and Metabolism,* 18, 238, (1998); Cheng et al., *J. Clin. Invest.,* 101, 1992 (1998); Yakovlev et al., *J Neuroscience,* 17, 7415 (1997); Rodriquez et al., *J. Exp. Med.,* 184, 2067 (1996); and Grobmyer et al., *Mol. Med.,* 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic and non-natural amino acid peptide inhibitors have been reported.

WO 96/40647 discloses ICE inhibitors of the formula:

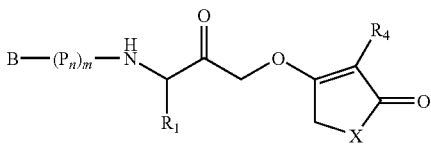

wherein B is H or an N-terminal blocking group; $R_1$ is the amino acid side chain of the $P_1$ amino acid residue wherein the $P_1$ amino acid is Asp; $P_n$ is an amino acid residue or a heterocyclic replacement of the amino acid wherein the heterocycle is defined in the application; $R_4$ is hydroxyl, alkoxyl, acyl, hydrogen, alkyl or phenyl; m is 0 or a positive integer; and X is N, S, O, or $CH_2$.

WO 97/22619 discloses inhibitors of interleukin-1β converting enzyme of the formula:

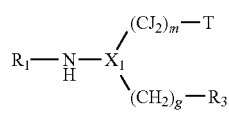

wherein $X_1$ is —CH; g is 0 or 1; each J is independently selected from the group consisting of —H, —OH, and —F, provided that when a first and second J are bound to a C and said first J is —OH, said second J is —H; m is 0, 1, or 2; T is, inter alia, —$CO_2H$; $R_1$ is

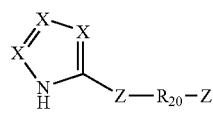

where each Z is independently CO or $SO_2$; $R_3$ is as defined in the application; each X is independently selected from the group consisting of =N— and =CH—; and $R_{20}$ is chosen from a group containing

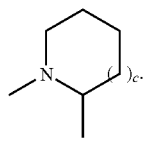

WO 98/16502 discloses aspartate ester inhibitors of interleukin-1β converting enzyme of the formula:

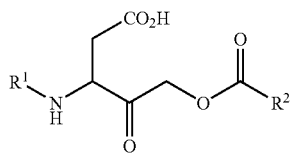

wherein $R^1$ is, inter alia, $R^5N(R^a)CHR^6CO$—; $R^2$ is certain groups; $R^6$ is H, $C_{1-6}$ alkyl, —$(CH_2)_n$aryl, —$(CH_2)_nCO_2R^a$, hydroxyl substituted $C_{1-6}$ alkyl, or imidazole substituted $C_{1-6}$ alkyl; each $R^a$ is independently hydrogen, $C_{1-6}$ alkyl or $(CH_2)_n$aryl; and $R^5$ is, inter alia, $CONR^aR^a$.

WO 99/18781 discloses dipeptide apoptosis inhibitors having the formula:

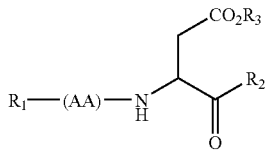

where $R_1$ is an N-terminal protecting group; AA is a residue of any natural α-amino acid, or β-amino acid; $R_2$ is H or $CH_2R_4$ where $R_4$ is an electronegative LG such as F, Cl, TsO—, MeO—, ArO—, ArCOO—, ArN— and ArS—; and $R_3$ is alkyl or H.

WO 99/047154 discloses dipeptide apoptosis inhibitors having the formula:

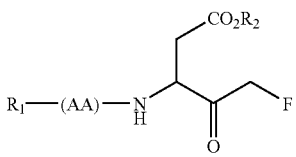

where $R_1$ is an N-terminal protecting group; AA is any non-natural amino acid or amino acid residue; and $R_2$ is an optionally substituted alkyl or H as defined in the application.

WO 00/023421 discloses (substituted) acyl dipeptide apoptosis inhibitors having the formula:

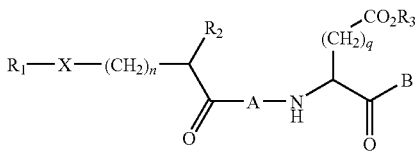

where n is 0, 1, or 2; q is 1 or 2; A is a residue of any natural or non-natural amino acid; B is a hydrogen atom, a deuterium atom, Cl-10 straight chain or branched alkyl, cycloalkyl, phenyl, substituted phenyl, naphthyl, substituted naphthyl, 2-benzoxazolyl, substituted 2-oxazolyl, $(CH_2)_m$cycloalkyl, $(CH_2)_m$phenyl, $(CH_2)_m$(substituted phenyl), $(CH_2)_m$(1- or 2-naphthyl), $(CH_2)_m$heteroaryl, halomethyl, $CO_2R_{13}$, $CONR_{14}R_{15}$, $CH_2ZR_{16}$, $CH_2OCO$aryl, $CH_2OCO$(substituted aryl), $CH_2OCO$(heteroaryl), $CH_2OCO$(substituted heteroaryl), or $CH_2OPO(R_{17})R_{18}$, where $R_{13}$, $R_{14}$, $R_{15}$, $R_{16}$, $R_{17}$, $R_{18}$ and m are as defined in the application; $R_2$ is selected from a group consisting of hydrogen, alkyl, cycloalkyl, phenyl, substituted phenyl, and $(CH_2)_mNH_2$; $R_3$ is hydrogen, alkyl, cycloalkyl, (cycloalkyl)alkyl, phenylalkyl, or substituted phenylalkyl; X is $CH_2$, C=O, O, S, NH, C(=O) NH or $CH_2OCONH$; and Z is an oxygen or a sulfur atom.

WO 00/061542 discloses dipeptide apoptosis inhibitors having the formula:

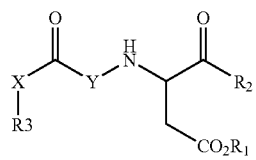

where $R_1$ is an optionally substituted alkyl or hydrogen group; $R_2$ is hydrogen or optionally substituted alkyl; Y is a residue of a natural or non-natural amino acid; $R_3$ is an alkyl, saturated carbocyclic, partially saturated carbocyclic, aryl, saturated heterocyclic, partially saturated heterocyclic or heteroaryl group, wherein said group is optionally substituted; and X is O, S, $NR_4$, or $(CR_4R_5)_n$ where $R_4$ and $R_5$ are, at each occurrence, independently selected from the group consisting of hydrogen, alkyl and cycloalkyl, and n is 0, 1, 2, or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted; or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and provided that when X is O, then $R_3$ is not unsubstituted benzyl or t-butyl; and when X is $CH_2$, then $R_3$ is not H.

Generally, the term tumor necrosis factor (TNF) refers to two closely related cytokines (encoded by separate genes) known as tumor necrosis factor-alpha (TNF, cachectin) and tumor necrosis factor-beta (lymphotoxin, TNF-beta). Both cytokines interact with the same cell membrane receptors, and both have been implicated as pathogenic mediators of human illness.

TNF-alpha participates in the signaling pathways that regulate cell apoptosis and inflammation. TNF-alpha is also known as TNFSF2, TNFA and DIF. TNF-alpha is a pro-inflammatory mammalian protein capable of inducing cellular effects by virtue of its interaction with specific cellular receptors. It is produced primarily by activated monocytes and macrophages. Lipopoly-sacccharide (LPS, also called endotoxin), derived from the cell wall of gram negative bacteria, is a potent stimulator of TNF-alpha synthesis.

Due to the deleterious effects which can result from an over-production or an unregulated production of TNF-alpha, considerable efforts have been made to regulate the serum level of TNF-alpha. The pathology of a number of diseases are affected by TNF-alpha, including, restinosis, inflammatory diseases of the central nervous system, demyelinating diseases of the nervous system, multiple sclerosis, septic arthritis, aneurysmal aortic disease, traumatic joint injury, peridontal disease, macular degeneration, diabetic retinopathy, occular inflammation, keratoconus, Sjogren's syndrome, corneal graft rejection, cachexia, and anorexia.

While a number of caspase and TNF-alpha inhibitors have been reported, it is not clear whether they possess the appropriate pharmacological properties to be therapeutically useful. Therefore, there is a continued need for small molecule caspase and TNF-alpha inhibitors that are potent, stable, and have good penetration through membranes to provide effective inhibition of apoptosis in vivo. Such compounds would be extremely useful in treating the aforementioned disease states where caspase enzymes and/or TNF-alpha cytokines play a role.

SUMMARY OF THE INVENTION

It has now been found that compounds of this invention and pharmaceutical compositions thereof are particularly effective as inhibitors of caspases, regulators of TNF-alpha levels or activity and inhibitors of cellular apoptosis and inflammatory responses. These compounds have the general formula I:

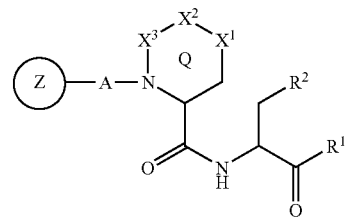

wherein:

$R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group, or a substituted non-aromatic heterocyclic group;

Y is an electronegative leaving group, $-OR$, $-SR$, $-OC=O(R)$, or $-OPO(R^3)(R^4)$;

$R^3$ and $R^4$ are independently R or OR;

$R^2$ is $CO_2H$, $CH_2CO_2H$, or optionally substituted esters, amides or isosteres thereof;

A is C=O or $SO_2$;

$X^1$ is oxygen, sulfur, $-NH$, or $-CH_2$, wherein $-NH$ is optionally substituted by an alkyl group, a cycloalkyl group, a (cycloalkyl)alkyl group, an amino acid N-terminal protecting group, or COR and $-CH_2$ is optionally substituted by fluorine, an alkyl group, a cycloalkyl group, a (cycloalkyl) alkyl group, an aralkyl group, an aryl group, an alkyloxy group, an alkylthioxy group, an aryloxy group, an arylthioxy group, an oxo group (i.e., =O), or a NHCOR group;

$X^2$ is oxygen, sulfur, $-NH$, or $-CH_2$, wherein $-NH$ is optionally substituted by an alkyl group, or an amino acid N-terminal protecting group and $-CH_2$ is optionally substituted by an alkyl group, an aryl group, an alkyloxy group, an alkylthioxy group, an aryloxy group, an arylthioxy group, or an oxo (i.e., =O) group, a NHCOR group; $X^1$ and $X^2$ optionally form part of a phenyl ring that is fused to the adjoining ring Q;

$X^3$ is $CH_2$ or $X^2$ and $X^3$ optionally form part of a phenyl ring that is fused to the adjoining ring Q, provided that when $X^2$ forms a ring with $X^3$, then $X^2$ does not form a ring with $X^1$;

any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon.

The compounds of this invention are potent inhibitors of caspase and TNF activity. They have inhibiting activity across a range of caspase targets with good efficacy in cellular models of apoptosis and inflammation. In addition, these compounds are expected to have improved cell penetration and pharmacokinetic properties and, as a consequence of their potency, have improved efficacy against diseases where caspases and/or TNF-alpha are implicated.

The invention also relates to methods for inhibiting the release of TNF-alpha from various cells or decreasing TNF-alpha levels or activity using the compounds and compositions of this invention. The invention also relates to methods for identifying agents useful for decreasing TNF-alpha levels or activity and treating TNF-alpha mediated diseases. The invention additionally relates to kits comprising a compound or composition of this invention and a tool for measuring TNF-alpha levels or activity.

DETAILED DESCRIPTION OF THE INVENTION

This invention provides novel compounds and pharmaceutically acceptable derivatives thereof that are particularly effective as caspase inhibitors and/or regulators of TNF-alpha levels or activity. The invention also provides methods for using the compounds to treat caspase and/or TNF-alpha mediated disease states in mammals. The compounds have the general formula I:

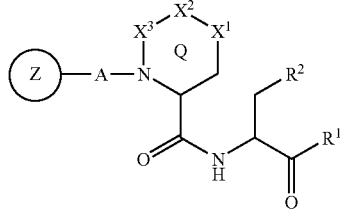

wherein:

$R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group, or a substituted non-aromatic heterocyclic group;

Y is an electronegative leaving group, $-OR$, $-SR$, $-OC=O(R)$, or $-OPO(R^3)(R^4)$;

$R^3$ and $R^4$ are independently R or OR;

$R^2$ is $CO_2H$, $CH_2CO_2H$, or optionally substituted esters, amides or isosteres thereof;

A is $C=O$ or $SO_2$;

$X^1$ is oxygen, sulfur, $-NH$, or $-CH_2$, wherein $-NH$ is optionally substituted by an alkyl group, a cycloalkyl group, a (cycloalkyl)alkyl group, an amino acid N-terminal protecting group, or COR and $-CH_2$ is optionally substituted by fluorine, an alkyl group, a cycloalkyl group, a (cycloalkyl) alkyl group, an aralkyl group, an aryl group, an alkyloxy group, an alkylthioxy group, an aryloxy group, an arylthioxy group, an oxo group (i.e., $=O$), or a NHCOR group;

$X^2$ is oxygen, sulfur, $-NH$, or $-CH_2$, wherein $-NH$ is optionally substituted by an alkyl group or an amino acid N-terminal protecting group and $-CH_2$ is optionally substituted by an alkyl group, an aryl group, an alkyloxy group, an alkylthioxy group, an aryloxy group, an arylthioxy group, or an oxo (i.e., $=O$) group, a NHCOR group; $X^1$ and $X^2$ optionally form part of a phenyl ring that is fused to the adjoining ring Q;

X is $CH_2$ or $X^2$ and $X^3$ optionally form part of a phenyl ring that is fused to the adjoining ring Q, provided that when $X^2$ forms a ring with $X^3$, then $X^2$ does not form a ring with $X^1$;

any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon.

As used herein, the following definitions shall apply unless otherwise indicated. The term "condition" or "state" refers to any disease, disorder or effect that produces deleterious biological consequences in a subject.

According to this invention, "TNF" or "TNF alpha" refers to TNF-alpha.

The term "subject" refers to an animal, or to one or more cells derived from an animal. Preferably, the animal is a mammal, most preferably a human. The cells can be in any form, including but not limited to cells retained in tissue, cell clusters, immortalized cells, transfected or transformed cells, and cells derived from an animal that have been physically or phenotypically altered.

The term "patient" as used in this application refers to any mammal, preferably humans.

The term "interferon gamma inducing factor" or "IGIF" refers to a factor which is capable of stimulating the endogenous production of IFN-γ.

The term "aliphatic" means straight chain, branched or cyclic $C_1$-$C_{12}$ hydrocarbons which are completely saturated or contain one or more units of unsaturation. For example, suitable aliphatic groups include substituted or unsubstituted linear, branched or cyclic alkyl, alkenyl, or alkynyl groups and hybrids thereof such as (cycloalkyl)alkyl, (cycloalkenyl) alkyl and (cycloalkyl)alkenyl. The term "alkyl" used alone or as part of a group or larger moiety refers to both straight and branched chains containing one to twelve carbon atoms.

The term "halogen" means F, Cl, Br, or I. The term "heteroatom" means nitrogen, oxygen or sulfur and shall include any oxidized form of nitrogen and sulfur, such as N(O), S(O), and $S(O)_2$ and the quaternized form of nitrogen. It is stood that the compounds of the present invention are limited to those existing in nature or chemically stable.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

The term "aryl", used alone or as part of a group or larger moiety, refers to monocyclic or polycyclic aromatic carbon ring systems, and monocyclic or polycyclic heteroaromatic ring systems containing one or more heteroatoms, having five to fourteen atoms. Such groups include, but are not limited to, phenyl, naphthyl, anthryl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, tetrahydrofuranyl, phthalimidinyl, tetrazolyl, and chromanyl.

The term "aralkyl" refers to an alkyl substituted by an aryl group. The term "heteroaryl" refers to an aryl group containing one or more heteroatoms. The term "heteroaralkyl" refers to an aralkyl group containing one or more heteroatoms.

The term "heterocyclic group" or "heterocycle" refers to saturated and unsaturated monocyclic or polycyclic ring systems containing one or more heteroatoms and with a ring size of three to eight. Such groups include, but are not restricted to, aziranyl, oxiranyl, azetidinyl, tetrahydrofuranyl, pyrrolinyl, pyrrolidinyl, dioxolanyl, imidazolinyl, imidazolidinyl, pyrazolinyl, pyrazolidinyl, pyranyl, piperidinyl, dioxanyl, morpholinyl, dithianyl, thiomorpholinyl, piperazinyl, trithianyl, quinuclidinyl, oxepanyl, and thietanyl. The term "heterocyclic ring", whether saturated or unsaturated, also refers to rings that are optionally substituted. The term "heterocyclylalkyl" refers to an alkyl group substituted by a heterocyclic ring.

The term "carbocyclic group" or "carbocyclyl" refers to saturated or unsaturated non-aromatic monocyclic or polycyclic carbon ring systems which can be fused to aryl or heterocyclic groups. Examples could include cyclohexyl, cyclopentyl, cyclobutyl, cyclopropyl, indanyl, tetrahydronaphthyl and the like. The term "carbocyclylalkyl", refers to an alkyl substituted by a carbocyclic group.

An aryl group (including a heteroaryl) or an aralkyl (including a heteroaralkyl) group, such as benzyl or phenethyl, can contain one or more substituents. Examples of suitable substituents of an aryl or aralkyl group include halogen, $CF_3$, —$R^5$, —$OR^5$, —OH, —SH, —$SR^5$, protected OH such as acyloxy and those described in Wuts and Greene, *Protective Groups in Organic Synthesis*, $3^{rd}$ Edition John Wiley & Sons, 1999), —$NO_2$, —CN, —$NH_2$, —$NHR^5$, —$N(R^5)_2$, —NHCOR$^5$, —NHCONHR$^5$, —NHCON(R$^5$)$_2$, —NR$^5$COR$^5$, —NHCO$_2$R$^5$, —CO$_2$R$^5$, —CO$_2$H, —COR$^5$, —CONHR$^5$, —CON(R$^5$)$_2$, —S(O)$_2$R$^5$, —SONH$_2$, —S(O)R$^5$, —SO$_2$NHR$^5$, or —NHS(O)$_2$R$^5$, where R$^5$ is an aliphatic or a substituted aliphatic group, preferably having one to three carbons, or an aryl or a substituted aryl group, with the proviso that when R$^5$ is an substituted aryl group, said aryl can not be substituted by an substituted aryl.

An aliphatic group or a non-aromatic heterocyclic ring can contain one or more substituents. Examples of suitable substituents of an aliphatic group or a non-aromatic heterocyclic ring include those listed above for an aryl or aralkyl group as well as the following: =O, =S, =NNHR$^6$, =NN(R$^6$)$_2$, =N—OR$^6$, =NNHCOR$^6$, =NNHCO$_2$R$^6$, =NNHSO$_2$R$^6$, and =NR$^6$, wherein R$^6$ is an aliphatic group or a substituted aliphatic group.

A substitutable nitrogen on an aromatic or non-aromatic heterocyclic ring can be optionally substituted. Suitable substituents on the nitrogen include R$^6$, COR$^6$, S(O)$_2$R$^6$, and CO$_2$R$^6$.

The term "electronegative leaving group" has the definition known to those skilled in the art (see March, *Advanced Organic Chemistry*, $4^{th}$ Edition, John Wiley & Sons, 1992). Examples of electronegative leaving groups include halogens such as F, Cl, Br, and I, aryl- and alkyl-sulfonyloxy groups, trifluoro-methanesulfonyloxy, OR$^7$, SR$^7$, —OC=O(R$^7$), —OPO(R$^8$)(R$^9$), where R$^7$ is an aliphatic group, an aryl group, an aralkyl group, a carbocyclic group, a carbocyclylalkyl group, a heterocyclic group, or an heterocyclylalkyl group; and R$^8$ and R$^9$ are independently R$^7$ or OR$^7$.

The term "amino acid N-terminal protecting group" has the definition known to those skilled in the art. Examples of amino acid N-terminal protecting groups include those described in Wuts and Greene, *Protective Groups in Organic Synthesis*, $3^{rd}$ Edition John Wiley & Sons, 1999).

Isosteres or bioisosteres of carboxylic acids and esters result from the exchange of an atom or a group of atoms to create a new compound with similar biological properties to the parent carboxylic acid or ester. The bioisosteric replacement can be physicochemically or topologically based. An example of an isosteric replacement for a carboxylic acid is CONHSO$_2$J where J is an alkyl group such as methyl, ethyl, propyl, butyl, and the like.

Compounds of this invention where R$^2$ is CO$_2$H or CH$_2$CO$_2$H, γ-ketoacids or δ-ketoacids respectively, can exist in solution as either the open form (a) or the cyclized hemiketal form (b) (y=1 for γ-ketoacids, y=2 for δ-ketoacids). The representation herein of either isomeric form is meant to include the other.

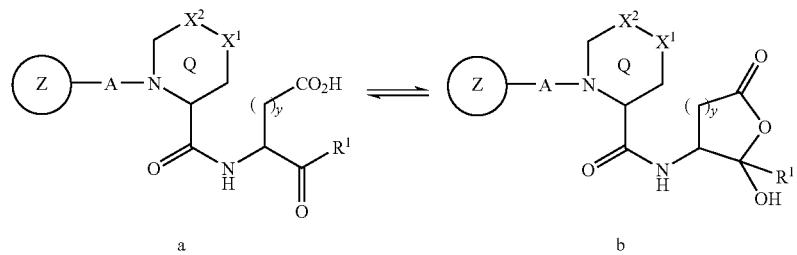

a                              b

Likewise it will be apparent to one skilled in the art that certain compounds of this invention can exist in tautomeric forms or hydrated forms, all such forms being within the scope of the invention. Unless otherwise stated, structures depicted herein are also meant to include all stereochemical forms of the structures; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of the application.

A preferred $R^1$ group is $CH_2Y$ where Y is an electronegative leaving group, OR, SR, or —OC(=O)(R) and most preferably Y is F.

Preferably $R^2$ is $CO_2H$, esters, amides or isosteres thereof.

$X^1$ is preferably $CH_2$; $X^2$ is preferably $CH_2$; or $X^1$ and $X^2$ combine to form part of an optionally substituted phenyl ring fused to ring Q. More preferably $X^1$ and $X^2$ are both $CH_2$.

A is preferably CO.

Z is preferably an optionally substituted aryl which is connected to A at a ring carbon.

Representative examples of compounds of the present invention are shown below in Table 1.

TABLE 1

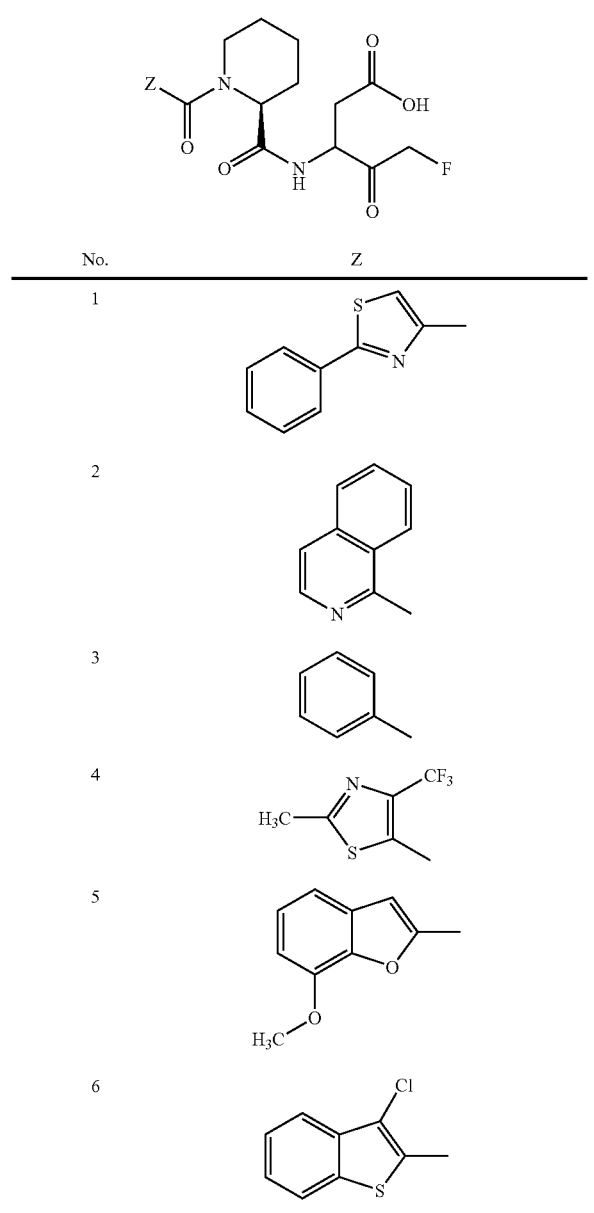
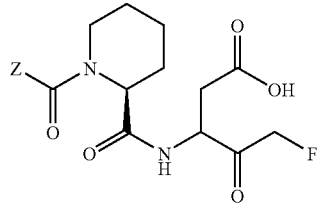

TABLE 1-continued

Representative Compounds

| No. | Z |
|---|---|
| 16 | 5-chloro-3-chloro-2-methyl-benzothiophene |
| 17 | 3-chloro-7-chloro-2-methyl-benzothiophene |
| 18 | 2-methyl-4-oxo-1H-quinoline |
| 19 | N-[(1H-indol-3-yl)methyl]-4-methylaniline |
| 20 | 1-benzyl-3-methyl-1H-indole |
| 21 | 5-(trifluoromethyl)-1-(3-methylbenzyl)pyridin-2(1H)-one |

TABLE 1-continued

Representative Compounds

| No. | Z |
|---|---|
| 22 | 3-methylphenyl phenyl sulfoxide |
| 23 | 2-(benzylthio)-6-methylpyrazine |
| 24 | 1-benzyl-3-methylbenzene |
| 25 | methylcyclohexane |

The compounds of this invention can be prepared in general by methods known to those skilled in the art for analogous compounds, as illustrated by the general Schemes I and II below and by the preparative examples that follow.

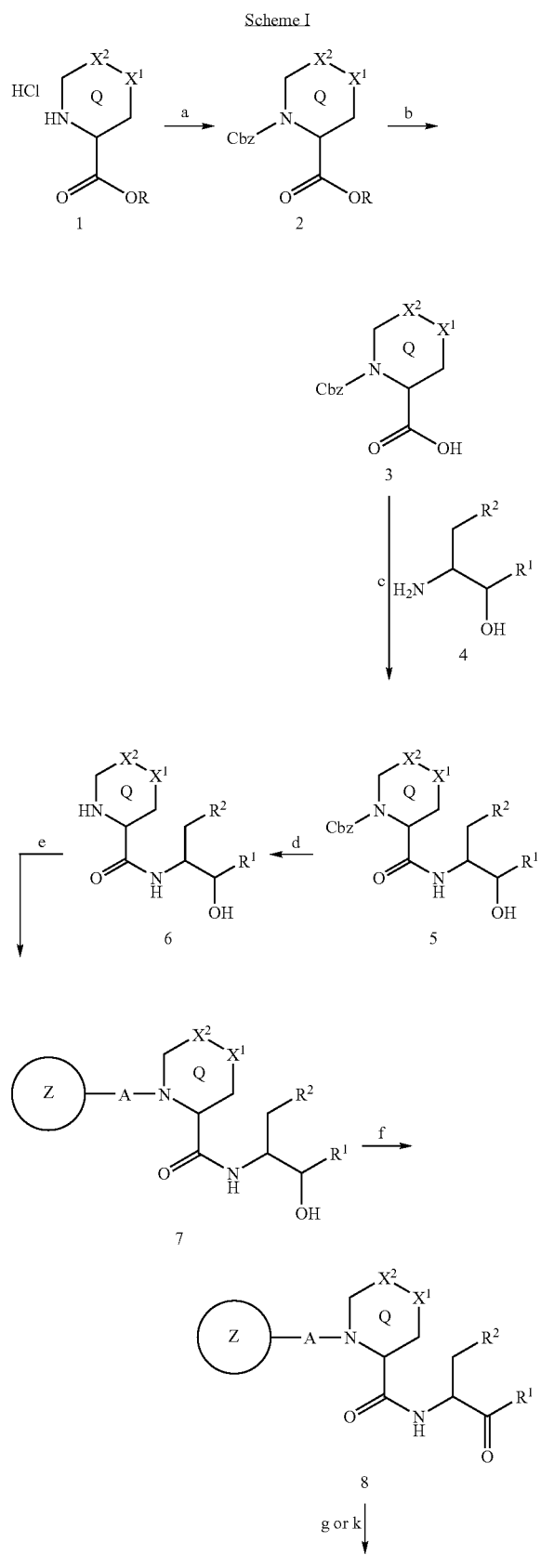

Reagents: (a) CbzOSuc/THF/TEA; (b) LiOH/THF/H$_2$O; (c) EDC/DMAP/HOBt; (d) H$_2$/10% Pd on C/EtOAc; (e) TBTU/DIPEA/DMF; (f) Dess-Martin periodinane; (g) TiCl$_4$/DCM; and (k) TFA/DCM.

Scheme I shows a general approach for making the present compounds. The starting ester hydrochloride 1 is first protected as a carbamate using a known amino acid N-protecting protocol, for example Cbz-OSuc (benzyloxycarbonyl-O-succinimidyl) in THF (tetrahydrofuran) in the presence of base, such as TEA (triethylamine, step a). The ester 2 is then hydrolyzed using base or, when the ester is a t-butyl group, using trifluoroacetic acid (TFA). The acid 3 is then coupled with the amino alcohol 4, using for example, EDC (1-(3-dimethylaminopropyl)-3-ethylcarbodiimide hydrochloride), DMAP (4-dimethylaminopyridine) and HOBt (1-hydroxybenzotriazole), to provide 5. Depending on the nature of $R^1$ and $R^2$, an amino ketone can be used in place of 4, which avoids the subsequent oxidation step. In the case of fluoromethyl ketones where $R^1$ is CH$_2$F, the amino alcohol 4 can be obtained according to the method of Revesz et al., *Tetrahedron Lett.*, 1994, 35, 9693. The carbamate 5 is then deprotected using catalytic hydrogenation, for example, H$_2$ with Pd on C in EtOAc (ethyl acetate), or acidolysis. The amine 6 is then N-substituted with the desired acylating or sulfonylating agent using standard methods as shown, for example, by step e, TBTU (2-(1H-benzotriazol-1-yl)-1,1,3,3-tetramethyluronium tetrafluoroborate) in DMF (dimethylformamide) in the presence of DIPEA (diisopropylethylamine). The hydroxyl group in compound 7 is then oxidized by standard methods as shown, for example, by step f. Finally, compound 8 is treated appropriately according to the nature of $R^2$ to generate I, using TiCl$_4$ in DCM (dichloromethane) or TFA in DCM. For example, if I requires $R^2$ to be a carboxylic acid, then $R^2$ in 4 is preferably an ester and the final step in the scheme is hydrolysis.

Scheme II

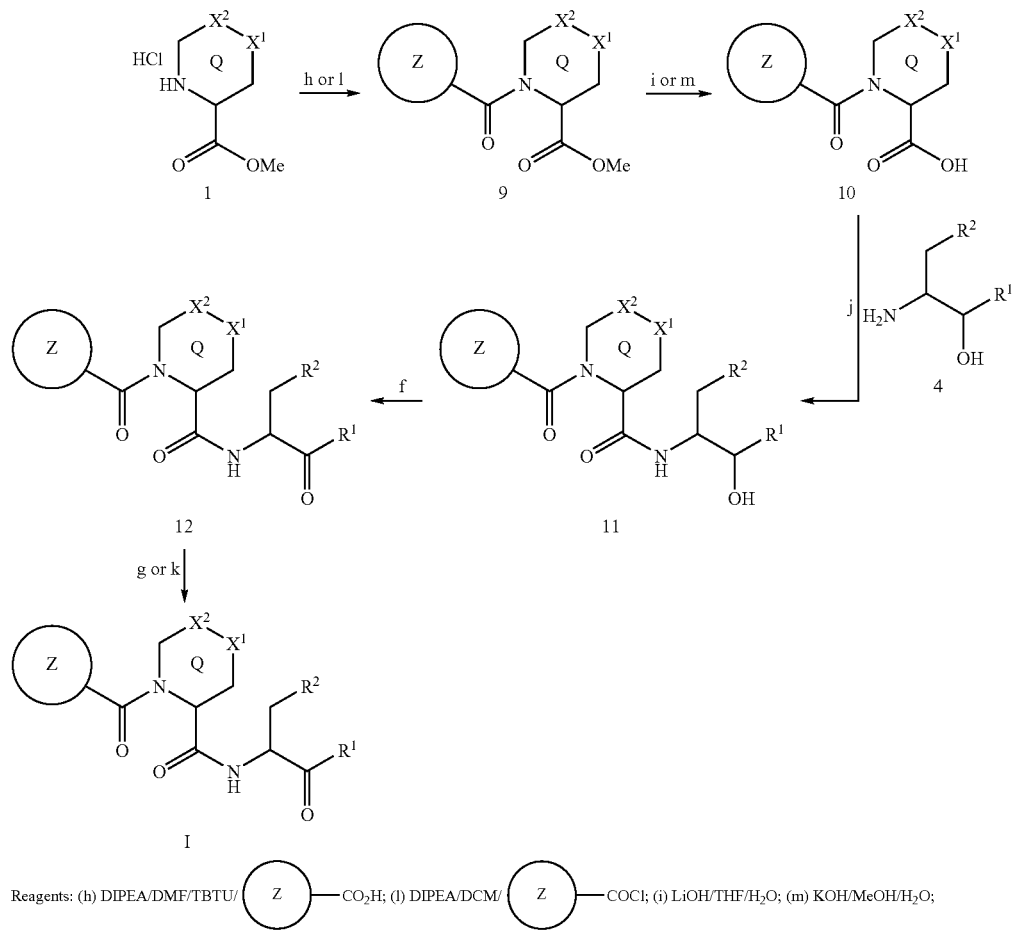

Reagents: (h) DIPEA/DMF/TBTU/ Z—CO₂H; (l) DIPEA/DCM/ Z—COCl; (i) LiOH/THF/H₂O; (m) KOH/MeOH/H₂O; (j) EDC/DMAP/HOBt; (f) Dess-Martin periodinane; (g) TiCl₄/DCM; and (k) TFA/DCM.

Scheme II represents an alternative approach for making the present compounds. The starting ester hydrochloride 1 is first reacted with either a carboxylic acid or an acid chloride using known amide bond forming reactions. The amide 9 is then hydrolyzed using base. The acid 10 is then coupled with the amino alcohol 4 to provide 11. Depending on the nature of $R^1$ and $R^2$, an amino ketone can be used in place of 4, which avoids the subsequent oxidation step. In the case of fluoromethyl ketones where $R^1$ is $CH_2F$, the amino alcohol 4 can be obtained according to the method of Revesz et al., *Tetrahedron Lett.*, 1994, 35, 9693. The hydroxyl group in compound 11 is then oxidized by standard methods as shown, for example, by step f. Finally compound 12 is treated appropriately according to the nature of $R^2$ to generate I. For example, if I requires $R^2$ to be a carboxylic acid, then $R^2$ in 4 is preferably an ester and the final step in the scheme is hydrolysis.

Certain compounds of this invention can be obtained as follows. The parent heterocyclic esters 1 or their acids or derivatives used in scheme I are either commercially available or can be prepared using standard methods. For example, the parent heterocyclic ester 1 where $X^{1-2}$ are each $CH_2$ is commercially available (H-homoproline-OMe). The parent heterocyclic ester 1, where $X^1$ is $CH_2$; and $X^2$ is oxygen, can be prepared by standard methods (Wolfe et al., *Tetrahedron Lett.*, 1979, 3913). The parent heterocyclic ester 1, where $X^1$ is $CH_2$ and $X^2$ is sulfur, can be prepared by standard methods (Miyazaki et al., *Bull. Chem. Soc. Jpn.*, 1993, 66, 536). The parent heterocyclic ester 1, where $X^2$ is $CH_2$; and $X^1$ is oxygen, can be prepared by standard methods (Kogami et al., *Bull. Chem. Soc. Jpn.*, 1987, 60, 2963; Asher et al., *Tetrahedron Lett.*, 1981, 141; and Brown et al., *J. Chem. Soc. Perkin Trans. I*, 1985, 2577). The Fmoc N-protected amino acid is also commercially available. The parent heterocyclic ester 1, where $X^2$ is $CH_2$; and $X^1$ is sulfur, can be prepared by standard methods (Kogami et al., *Bull. Chem. Soc. Jpn.*, 1987, 60, 2963; and Sakai et al., *Chem. Pharm. Bull.*, 1981, 29, 1554). The corresponding free amino acid is also commercially available. The parent heterocyclic esters 1, where $X^{1-2}$ is $CH_2$ and have various substituents can be prepared by standard methods (Shuman et al., *J. Org. Chem.*, 1990, 55, 738; Agami et al., *Synlett*, 1997, 799; and Nazih et al., *Synlett*, 1998, 1337).

The compounds of this invention are designed, inter alia, to inhibit caspase activity and/or decrease TNF-alpha levels or activity. These compounds can be assayed, for example, for their ability to inhibit apoptosis, inhibit the release of IL-1β, inhibit caspase activity, and/or decrease TNF-alpha levels or activity. Assays for each of the activities are known in the art and are described below in detail in the Examples. Accordingly, these compounds are capable of targeting and inhibiting events in caspase- (for example, IL-1-), apoptosis-, IGIF-, IFN-γ-, and TNF-α-mediated diseases, and the ultimate activity of the relevant protein in inflammatory diseases, autoimmune diseases, destructive bone, proliferative disorders, infectious diseases, and degenerative diseases.

Compounds of this invention also inhibit conversion of pro-IGIF into active, mature IGIF by inhibiting ICE. The term "interferon gamma inducing factor" or "IGIF" refers to a factor which is capable of stimulating the endogenous production of IFN-γ.

Because ICE is essential for the production of mature IGIF (IL-18), inhibition of ICE effectively blocks initiation of IGIF-mediated physiological effects and symptoms, by inhibiting production of mature IGIF. IGIF is in turn essential for the production of IFN-γ. ICE therefore effectively blocks initiation of IFN-γ-mediated physiological effects and symptoms, by inhibiting production of mature IGIF and thus production of IFN-γ.

Compounds of this invention also inhibit the release of TNF-alpha from activated cells.

The pharmaceutical compositions and methods of this invention, therefore, will be useful for controlling caspase and TNF-alpha activity in vivo. The compositions and methods of this invention will thus be useful for controlling caspase, IL-1, IGIF, IFN-γ, or TNF-alpha levels in vivo and for treating or reducing the advancement, severity or effects of caspase, IL-1-, apoptosis-, IGIF-, IFN-γ-, or TNF-alpha mediated conditions, including diseases, disorders or effects.

According to another embodiment, the invention provides a composition comprising a compound of this invention or a pharmaceutically acceptable derivative thereof, as described above, and a pharmaceutically acceptable carrier.

According to another embodiment, the compositions of this invention can further comprise another therapeutic agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound.

The term "pharmaceutically acceptable carrier" refers to a non-toxic carrier that can be administered to a patient, together with a compound of this invention, and which does not destroy the pharmacological activity thereof.

Pharmaceutically acceptable carriers that can be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any pharmaceutically acceptable salt, ester, salt of an ester or other derivative of a compound of this invention which, upon administration to a recipient, is capable of providing, either directly or indirectly, a compound of this invention or an inhibitory active metabolite or residue thereof. The methods for preparing salts or esters of a compound of this invention are known to one of skill in the art.

Pharmaceutically acceptable derivatives of the compounds of this invention include, without limitation, esters, amino acid esters, phosphate esters, metal salts and sulfonate esters.

In pharmaceutical compositions comprising only a compound of formula I as the active component, methods for administering these compositions can additionally comprise the step of administering to the subject an additional agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound. When a second agent is used, the second agent can be administered either as a separate dosage form or as part of a single dosage form with the compounds or compositions of this invention.

The amount of compound present in the above-described compositions should be sufficient to cause a detectable decrease in the severity of the disease, in caspase activity and/or cell apoptosis, or in TNF-alpha activity and/or cell apoptosis as measured by any of the assays described in the Examples.

The compounds of this invention can be employed in a conventional manner for controlling IGIF and IFN-γ levels in vivo and for treating diseases or reducing the advancement or severity of effects which are mediated by a caspase, IL-1, apoptosis, IGIF, IFN-γ or TNF-alpha. Such methods of treatment, their dosage levels and requirements can be selected by those of ordinary skill in the art from available methods and techniques.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention can also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

According to a preferred embodiment, the compositions of this invention are formulated for pharmaceutical administration to a mammal, preferably a human being.

Such pharmaceutical compositions of the present invention can be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection and infusion techniques. Preferably, the compositions are administered orally or intravenously.

Sterile injectable forms of the compositions of this invention can be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil and castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

If a solid carrier is used, the preparation can be tableted, placed in a hard gelating capsule in powder or pellet form, or in the form of a troche or lozenge. The amount of solid carrier will vary, e.g., from about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

A syrup formulation can consist of a suspension or solution of the compound in a liquid carrier for example, ethanol, glycerine, or water with a flavoring or coloring agent. An aerosol preparation can consist of a solution or suspension of the compound in a liquid carrier such as water, ethanol or glycerine; whereas in a powder dry aerosol, the preparation can include e.g., a wetting agent.

Formulations of the present invention comprise an active ingredient together with one or more acceptable carrier(s) thereof and optionally any other therapeutic ingredient(s). The carrier(s) should be "acceptable" in the sense of being compatible with the other ingredients of the formulation and not deleterious to the recipient thereof.

The pharmaceutical compositions of this invention can be orally administered in any orally acceptable dosage form including, but not limited to, capsules, tablets, and aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, the pharmaceutical compositions of this invention can be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, the pharmaceutical compositions can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions can be formulated in an ointment such as petrolatum.

The pharmaceutical compositions of this invention can also be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents known in the art.

It will be recognized by one of skill in the art that the form and character of the pharmaceutically acceptable carrier or diluent is dictated by the amount of active ingredient with which it is to be combined, the route of administration, and other well-known variables.

The above-described compounds and compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a skin disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, contact dermatitis, scarring, graft vs host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, trauma, systemic inflammatory response syndrome, multiple organ dysfunction syndrome, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal chord injury, hepatitis-B, hepatitis-C, hepatitis-G, yellow fever, dengue fever, Japanese encephalitis, various forms of liver disease, renal disease, polycystic kidney disease, *H. pylori*-associated gastric and duodenal ulcer disease, HIV infection, tuberculosis, and meningitis.

The above-described compounds and compositions are also useful in therapeutic applications relating to a TNF mediated disease. The phrase "TNF-alpha mediated disease" means, all diseases states in which TNF-alpha plays a role, either by excessive production or release of TNF-alpha, itself, or by TNF-alpha causing an event that triggers or exacerbates the disease, such as production or release of another pathophysiological biochemical agent, or cytokine. In one preferred embodiment, TNF-alpha plays a direct role.

Such TNF-alpha mediated diseases can include, e.g., restinosis, inflammatory diseases such as inflammatory diseases of the central nervous system, demyelinating diseases of the nervous system, multiple sclerosis, septic arthritis, aneurysmal aortic disease, traumatic joint injury, peridontal disease, macular degeneration, diabetic retinopathy, occular inflammation, keratoconus, Sjogren's syndrome, corneal graft rejection, cachexia, and anorexia.

Excessive TNF-alpha tissue levels have been implicated in mediating or exacerbating a number of diseases including: rheumatoid arthritis, rheumatoid spondylitis, osteoarthritis, gouty arthritis and other arthritic conditions; also general sepsis, gram-negative sepsis, septic shock, endotoxic shock, toxic shock syndrome, adult respiratory distress syndrome (ARDS), cerebral malaria, chronic pulmonary inflammatory disease, silicosis, asbestosis, pulmonary sarcoidosis, bone resorption diseases, graft vs. host reactions, allograft rejections; also fever and myalgias due to bacterial or viral infections, such as influenza; cachexia secondary to acquired immune deficiency syndrome (AIDS), keloid formation, scar tissue formation, Crohns disease, ulcerative colitis, or pyresis; a number of "autoimmune diseases" such as multiple sclerosis, autoimmune diabetes, and systemic lupus erythematosus.

TNF-alpha inhibitors are useful in the treatment of a variety of allergic, traumatic and other injurious disorders including: asthma, chronic bronchitis, atopic dermatitis, urticaria, allergic rhinitis, allergic conjunctivitis, eosiniophilic granuloma, ulcerative colitis, Crohn's disease, reperfusion injury of the myocardium and brain, chronic glomerulonephritis, and adult respiratory distress syndrome (ARDS).

The compounds of this invention can inhibit the release of TNF-alpha and thus can be useful for inhibiting or blocking several pathophysiological effects of TNF-alpha at injury or surgery sites and thus also inhibit the release of other pathophysiological biochemical products from cells such as histamines, prostaglandins, bradykinins, and peroxidases.

As discussed above, TNF-alpha inhibitors can be very effective in the treatment of disorders which follow cellular, tissue or organ injury or surgery, and can be as effective, or even more potent, than corticosteroids or immunosuppressants without producing the side effects common to these agents.

This invention also relates to a therapeutic method of (1) inhibiting TNF-alpha release from cells and (2) preventing the untoward, toxic or lethal effects of excessively high tissue levels of TNF-alpha in a mammal, including a human. This method comprises administering to a mammal an effective TNF-alpha inhibiting quantity of one or more of the above compounds. This method also can be used for the prophylactic treatment or prevention of certain TNF-alpha mediated or exacerbated diseases amenable thereto. The invention provides a method for the treatment of allergic, traumatic, radiation, chemical, microbial and other injurious disorders by administering to a mammal, including a human, in need thereof an effective amount of such compounds.

The compounds, by inhibiting or blocking the release of TNF-alpha or decreasing TNF-alpha levels and activity, as well as the pathophysiologic actions of excessive levels of TNF-alpha in each of these circumstances, directly facilitate the arrest or resolution of the tissue or organ damage, and facilitates the restoration of normal function. Together, these actions relate their novel use in treating tissue trauma, or other injury disorders caused by infection, allergy, immunologic phenomena, burns, radiation exposure, neoplastic disease, toxic chemicals and expressed as cardiovascular damage, neurologic injury, renal damage, liver damage, pancreatic damage, as well as ascites, localized edema, dermal damage and dermal blister.

The term "inhibiting the release of TNF-α" means:

a) decrease of in vivo TNF-alpha levels in a mammal such as a human; or b) a down regulation of TNF-alpha levels in vitro or in vivo; or c) a down regulation of TNF-alpha activity, by inhibition of the direct synthesis of TNF-alpha or a post-translation event.

The compounds can be useful in inhibiting the release of TNF-alpha by monocytes, macrophages, neuronal cells, endothelial cells, epidermal cells, mesenchymal cells (for example: fibroblasts, skeletal myocytes, smooth muscle myocytes, cardiac myocytes) and many other types of cells.

The term "condition" or "state" refers to any disease, disorder or effect that produces deleterious biological consequences in a subject.

The level of TNF-alpha protein in the blood or cell of a patient or a cell culture (i.e., in the cells and/or in the culture media) can be determined by assaying for immunospecific binding to TNF-alpha or to proteins that are known to be produced as a result of the presence of active TNF-alpha. Such assays are known in the art. For example, the immunoassays which can be used include, but are not limited, to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, FACS analysis and protein A immunoassays. Such assays are well known in the art (see, e.g., Ausubel et al, eds, 1994, Current Protocols in Molecular Biology, Vol. 1, John Wiley & Sons, Inc., New York, which is incorporated by reference herein in its entirety).

Competitive binding assays can also be used to determine the level of TNF-alpha. One example of a competitive binding assay is a radioimmunoassay comprising the incubation of labeled proteins from cells expressing TNF-alpha (e.g., $^3$H or $^{125}$I) with a TNF-alpha antibody in the presence of increasing amounts of unlabeled TNF-alpha, and the detection of the TNF-alpha antibody bound to the labeled TNF-alpha.

TNF-alpha levels can also be assayed by activity assays known in the art. For example, samples of treated cell cultures or from blood from patients can be used in TNF-alpha activity assays known in the art, e.g., *J. Immunol. Methods*, 1995, 178, 71-76; *Burns*, 1994, 20(1), 40-44.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy.

Typically, the pharmaceutical compositions of this invention will be administered from about 1 to 5 times per day or alternatively, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic agents, both the compound and the additional agent should be present at dosage levels of between about 10% to 80% of the dosage normally administered in a monotherapy regime.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level, treatment should cease. Patients can, however, require intermittent treatment on a long-term basis upon any recurrence or disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

One embodiment of this invention provides a method for treating or preventing an IL-1-mediated disease or an apoptosis-mediated disease in a subject comprising the step of administering to the subject any compound, pharmaceutical composition, or combination described herein.

Another embodiment of this invention provides a method for inhibiting a caspase-mediated function in a subject comprising the step of administering to the subject any compound, pharmaceutical composition, or combination described.

Another embodiment of this invention provides a method for decreasing IGIF or IFN-γ production in a subject comprising the step of administering to the subject any compound, pharmaceutical composition, or combination described.

Another embodiment of this invention provides a method for treating complications associated with coronary artery bypass grafts in a subject comprising the step of administering to the subject any compound, pharmaceutical composition, or combination described herein.

Another embodiment of this invention provides a method for preserving cells comprising the step of bathing the cells in a solution of any compound described herein. Such method using caspase inhibitors has been reported [Schierle et al., *Nature Medicine*, 5, p. 97 (1999); and Natori et al., *Transplantation*, 68, pp. 89-96 (1999)]. The amount of caspase inhibitor needed will depend on the effectiveness of the inhibitor for a given cell type and the length of time required to preserve cells from apoptotic cell death.

Another embodiment of this invention provides a method for preserving cells needed for an organ transplant or for preserving blood products, using any compound, pharmaceutical composition, or combination described herein. Li et al., *Transfusion*, 40, pp. 1320-1329 (2000).

Another embodiment of this invention provides a method for treating various forms of cancer in a subject comprising the step of administering to the subject any compound, pharmaceutical composition, or combination described herein as a component of immunotherapy. Droin et al., *Oncogene*, 16, pp. 2885-2894 (1998); Boudard et al., *Leukemia*, 14, pp. 2045-2051 (2000); Faderl et al., *Clinical Cancer Research*, 5, pp. 4041-4047 (1999); Ozoren et al., *Cancer Research*, 60, pp. 6259-6265 (2000); Sasaki et al., *British Journal of Urology*, 81, pp. 852-855 (1998); and Hedlund et al., *Prostate*, 36, pp. 92-101 (1998).

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it can be delivered together with the compound of this invention in a single dosage form, or, as a separate dosage form. When administered as a separate dosage form, the other caspase inhibitor or agent can be administered prior to, at the same time as, or following administration of a pharmaceutically acceptable composition comprising a compound of this invention.

A kit according to this invention comprises a compound or a pharmaceutically acceptable derivative thereof or pharmaceutical composition of this invention and a tool for measuring TNF alpha levels and/or activity in vitro or in vivo. The kit can further comprise instructions for using the contents of the kit. A tool for measuring TNF-alpha levels of this invention refer to materials that can be used to measure the TNF gene product (i.e., RNA or protein) or activity. Such methods are described for example above. Thus, a tool according to this invention can include e.g., an anti-TNF antibody, a TNF-alpha DNA probe or a genetically engineered cell line responsive to TNF alpha levels described above.

The methods for identifying a compound or composition that decreases TNF-alpha activity and/or levels according to this invention include methods for screening of a plurality of compounds or compositions for their ability to decrease TNF-alpha activity and/or levels. For example, high-throughput screening is a desired embodiment of this invention. According to one embodiment of this invention, high-throughput screening can be achieved by having cells in culture in a plurality of wells in a microtiter plate, adding a different compound or composition to each well and comparing the TNF-alpha levels and/or activity in each cell culture to the TNF-alpha levels or activity present in a cell culture in a control well. Controls that are useful for the comparison step according to this invention include cells or subjects that have not been treated with a compound or composition and cells or subjects have been treated with a compound or composition that is known to have no effect on TNF-alpha levels or activity. According to one embodiment of this invention, the high throughput screening is automated so that the steps including the addition of the cells to the plate up to the data collection and analysis after addition of the compound or composition are done by machine. Instruments that are useful in the comparison step of this invention, e.g., instruments that can detect labeled objects (e.g., radiolabelled, fluorescent or colored objects) or objects that are themselves detectable, are commercially available and/or known in the art. Accordingly, compounds and compositions according to this invention that are useful for decreasing TNF-alpha levels and/or activity can be quickly and efficiently screened.

In order that this invention be more fully understood, the following preparative and testing examples are set forth. These examples are for the purpose of illustration only and are not to be construed as limiting the scope of the invention in any way.

EXAMPLES

Example 1

[3S/R (2S)]-5-Fluoro-4-oxo-3-[1-(2-phenyl-thiazole-4-carbonyl)-2-piperidinecarboxamido]-pentanoic acid (Compound 1)

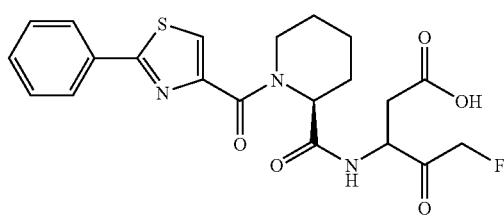

Method A: (S)-1-(Benzyloxycarbonyl) 2-piperidine-carboxylic acid methyl ester

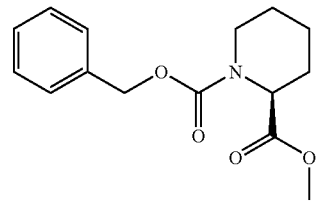

A stirred suspension of (S)-Piperidine-carboxylic acid methyl ester hydrochloride (2.00 g, 11.13 mmol) in anhydrous THF (40 ml) at room temperature was treated with triethylamine (3.41 ml, 24.50 mmol). The reaction mixture was stirred at room temperature for 30 min before the addition of N-(benzyloxycarbonyloxy)succinimide (3.05 g, 12.23 mmol). The resulting mixture was stirred for 2 hr, before being diluted with ethyl acetate (20 ml), washed with 2 N HCl, saturated aq. NaHCO$_3$, saturated aq. NaCl, dried (Na$_2$SO$_4$), filtered and concentrated. The residue was purified by flash chromatography (20% ethyl acetate in hexane) to afford the sub-title compound as a colourless oil (2.0085 g, 65%): $^1$H NMR (400 MHz, CDCl$_3$) δ 1.19-1.1.54 (2H, m), 1.58-1.80 (4H, m), 2.18-2.33 (1H, m), 2.90-3.15 (1H, m), 3.66-3.81 (3H, m), 4.03-4.21 (1H, m), 4.81-5.25 3H, m), 7.28-7.45 (5H, m).

Method B: (S)-1-(Benzyloxycarbonyl)-2-piperidine-carboxylic acid

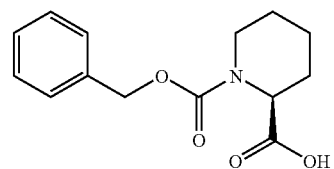

A stirred solution of (S)-1-(benzyloxy-carbonyl)-2-piperidinecarboxylic acid methyl ester (2.00 g, 7.21 mmol) in THF (20 ml) at room temperature was treated with water (10 ml). Lithium hydroxide (190 mg, 7.93 mmol) was added and the resulting mixture stirred at room temperature for 3 hr. An additional quantity of lithium hydroxide (40 mg, 1.67 mmol) was added and the resulting mixture was stirred for 2 hr prior to the removal of the organic solvent. The resulting solution was washed with diethyl ether and the remaining aqueous layer was made acidic with 2 N HCl prior to a second extraction step with ethyl acetate. The organic layer was then recovered, dried (Na$_2$SO$_4$), filtered and concentrated to reveal a colorless oil (1.9927 g, 105%) which crystallized upon standing: $^1$H NMR (400 MHz, CDCl$_3$) δ 1.30-1.88 (5H, m), 2.22-2.41 (1H, m), 3.00-3.21 (1H, m), 4.08-4.25 (1H, m), 4.91-5.30 (3H, m), 7.27-7.48 (5H, m).

Method C: [3S/R,4S/R,(2S)]-5-Fluoro-4-hydroxy-3-[1-(benzyloxycarbonyl)-2-piperidinecarboxamido]-pentanoic acid tert-butyl ester

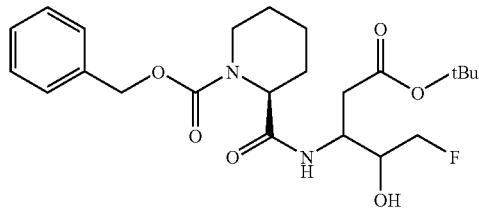

A stirred mixture of (S)-1-(benzyloxy carbonyl)-2-piperidinecarboxylic acid (4.82 g, 18.31 mmol), 3-amino-5-fluoro-4-hydroxy-pentanoic acid tert-butyl ester (3.99 g, 19.25 mmol), HOBt (2.72 g, 20.13 mmol), DMAP (2.57 g, 21.04 mmol) and anhydrous THF (60 ml) was cooled to 0° C. before EDC (3.86 g, 20.13 mmol) was added. The mixture was allowed to warm to room temperature over 16 hrs before being concentrated under reduced pressure. The residue was purified by flash chromatography (60% ethyl acetate in hexane) to afford the sub-title compound as a white foam (7.3754 g, 72%): $^1$H NMR (400 MHz, CDCl$_3$) δ 1.31-1.80 (14H, m), 2.20-2.38 (1H, m), 2.49-3.07 (3H, m), 3.11-3.70 (1H, m), 3.80-4.58 (4H, m), 4.70-5.28 (1H, m), 6.58-7.05 (1H, m), 7.23-7.48 (5H, m).

Method D: [3S/R,4S/R,(2S)]-5-Fluoro-4-hydroxy-3-[2-piperidinecarboxamido]-pentanoic acid tert-butyl ester

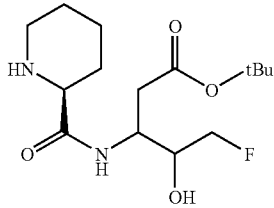

A stirred solution of [3S/R,4S/R,(2S)]-5-fluoro-4-hydroxy-3-[1-(benzyloxycarbonyl)-2-piperidinecarboxamido]-pentanoic acid tert-butyl ester (7.37 g, 16.29 mmol) in ethyl acetate (150 ml) was treated with 10% Pd/C (830 mg). The reaction mixture was then thoroughly degassed and placed under a hydrogen balloon. The resulting mixture was stirred at room temperature for 3 hrs after which it was filtered through celite and concentrated to the sub-title compound as a colorless gum (5.17 g, 100%): $^1$H NMR (400 MHz, CDCl$_3$) δ 1.16-2.00 (15H, m), 2.51-2.78 (3H, m), 2.99-3.09 (1H, m), 3.18-3.28 (1H, m), 3.93-4.56 (4H, m), 7.39-7.58 (1H, m); $^{19}$F (376 MHz, CDCl$_3$) δ −229.34 (t), −229.42 (t), −229.87 (t), 230.02 (t).

Method E: [3S/R,4S/R,(2S)]-5-Fluoro-4-hydroxy-3-[1-(2-phenyl-thiazole-4-carbonyl)-2-piperidine-carboxamido]-pentanoic acid tert-butyl ester

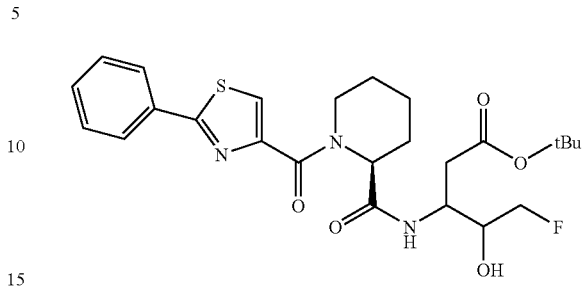

A stirred solution of [3S/R,4S/R,(2S)]-5-fluoro-4-hydroxy-3-[2-piperidinecarboxamido]-pentanoic acid tert-butyl ester (520 mg, 1.63 mmol), in DMF (9.7 ml) at room temperature was treated with DIPEA (311 μl, 1.80 mmol). The resulting mixture was allowed to stir for 30 min before being treated with 2-phenyl-thiazole-4-carboxylic acid (335 mg, 1.63 mmol) and TBTU (524 mg, 1.63 mmol). The mixture was stirred at room temperature for 16 hr and then diluted with ethyl acetate. The resulting solution was washed with 2 N HCl, saturated aq. NaHCO$_3$, saturated aq. NaCl, dried (Na$_2$SO$_4$), filtered and concentrated to reveal an oil. The residue was purified by flash chromatography (60% ethyl acetate in hexane) to afford the sub-title compound as a colorless oil (463 mg, 56%): $^1$H NMR (400 MHz, CDCl$_3$) δ 1.10-1.85 (15H, m), 2.22-2.89 (3H, m), 3.09-4.78 (6H, m), 5.20-5.43 (1H, m), 7.40-7.56 (3H, m), 7.81-8.11 (3H, m).

Method F: [3S/R,(2S)]-5-fluoro-4-oxo-3-[1-(2-phenyl-thiazole-4-carbonyl)-2-piperidinecarboxamido]-pentanoic acid tert-butyl ester

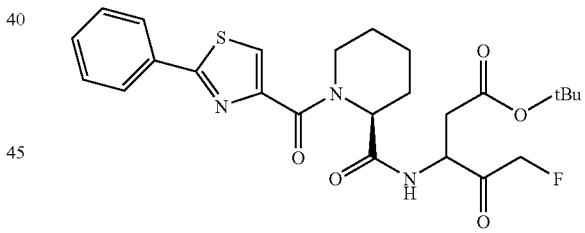

A stirred solution of [3S/R,4S/R,(2S)]-5-Fluoro-4-hydroxy-3-[1-(2-phenyl-thiazole-4-carbonyl)-2-piperidinecarboxamido]-pentanoic acid tert-butyl ester (462 mg, 0.91 mmol) in anhydrous DCM (25 ml) was treated with 1,1,1-triacetoxy-1,1-dihydro-1,2-benziodoxol-3(1H)-one (426 mg, 1.00 mmol) at 0° C. The resulting mixture was kept at 0° C. for 2 hr, diluted with DCM, and washed with saturated aq. Na$_2$S$_2$O$_3$.5H$_2$O, saturated aq. NaHCO$_3$, saturated aq. NaCl. dried (Na$_2$SO$_4$) and concentrated. The residue was purified by flash chromatography (33% ethyl acetate in hexane) to afford the sub-title compound as a white solid (376 mg, 82%): IR (solid) 1731, 1619, 1506, 1460, 1363, 1260, 1158 cm$^{-1}$; $^1$H NMR (400 MHz, CDCl$_3$) δ 1.16-1.81 (14H, m), 2.25-2.42 (1H, m), 2.69-3.25 (3H, m), 4.48-5.46 (5H, m), 7.36-8.32 (7H, m); $^{13}$C NMR (100 MHz, CDCl$_3$) δ 21.08, 21.29, 21.33, 25.24, 25.72, 27.23, 28.14, 36.60, 41.33, 41.52, 46.10, 46.27, 52.06, 52.77, 52.84, 82.25, 82.40, 82.66, 83.81, 85.68, 125.09, 125.49, 126.50, 126.69, 127.02, 127.10, 129.46, 129.55, 131.00, 131.18, 132.85, 133.04, 133.29, 150.75, 150.92, 163.50, 163.65, 165.17, 168.07, 168.14, 170.07, 170.23, 171.37, 202.87, 203.02; $^{19}$F (376 MHz, CDCl$_3$) δ −231.36, −231.69, −231.86, −232.28; MS (LR, ES) Calculated for C$_{25}$H$_{30}$FN$_3$O$_5$S: 503.5974.

Method G: [3S/R,(2S)]-5-Fluoro-4-oxo-3-[1-(2-phenyl-thiazole-4-carbonyl)-2-piperidinecarboxamido]-pentanoic acid

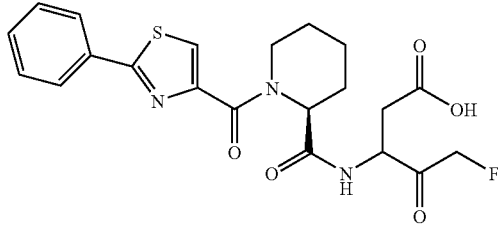

A stirred solution of [3S/R,(2S)]-5-fluoro-4-oxo-3-[1-(2-phenyl-thiazole-4-carbonyl)-2-piperidinecarboxamido]-pentanoic acid tert-butyl ester (370 mg, 0.73 mmol) in anhydrous DCM (20 ml) was treated with a 1 M solution of titanium tetrachloride in DCM (3.67 ml, 3.67 mmol) at −10° C. The resulting mixture was warmed to 0° C. and kept at this temperature for 1 hr. The reaction mixture was then diluted with DCM, and washed with 2 N HCl, saturated aq. NaCl, dried (Na$_2$SO$_4$) and concentrated. The residue was purified by reverse phase HPLC (acetonitrile/water) to afford the title compound as a white foam (102 mg, 31%): IR (solid) 1798, 1736, 1674, 1617, 1517, 1479, 1470, 1265; $^1$H NMR (400 MHz, d$_6$-DMSO+TFA) δ 1.18-1.79 (4H, m), 2.08-2.28 (1H, m), 2.42-3.50 (5H, m), 4.08-5.40 (4H, m), 7.45-8.28 (6H, m), 8.41-8.67 (1H, m); $^{13}$C NMR (100 MHz, d$_6$-DMSO+TFA) δ 19.07, 19.24, 23.29, 23.69, 25.63, 25.72, 26.42, 26.49, 31.54, 33.23, 43.65, 46.14, 50.81, 50.91, 51.56, 51.64, 56.26, 56.34, 80.07, 81.87, 81.97, 83.66, 83.75, 102.43, 102.47, 102.63, 102.66, 125.17, 125.24, 128.19, 129.52, 131.40, 149.51, 162.07, 162.61, 162.67, 165.34, 165.55, 169.71, 169.86, 170.64, 170.72, 171.75, 201.84, 201.20, 201.34; $^{19}$F (376 MHz, d$_6$-DMSO) δ −226.74, −226.82, −226.84, −227.00, −230.37, −230.60, −230.83, −232.41, −232.55, −232.62, −232.7; MS (LR, ES) calculated for C$_{21}$H$_{22}$FN$_3$O$_5$S: 447.4890, ES− 446.408, ES+ 448.184.

Example 2

[3S/R (2S)]-5-Fluoro-4-oxo-3-[1-(isoquinoline-1-carbonyl)-2-piperidinecarboxamido]-pentanoic acid, trifluoroacetic acid salt (compound 2)

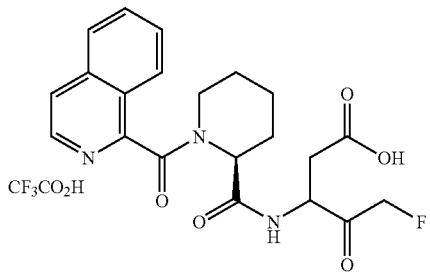

Method H: (S)-1-(Isoquinoline-1-carbonyl)-2-piperidinecarboxylic acid methyl ester

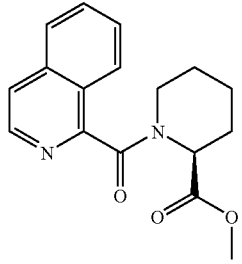

A stirred solution of (S)-1-Piperidine-carboxylic acid methyl ester hydrochloride (1.00 g, 5.57 mmol), in DMF (20 ml) at room temperature was treated with DIPEA (2.12 ml, 12.25 mmol). The resulting mixture was allowed to stir for 30 min before being treated with 1-isoquinolinecarboxylic acid (964 mg, 5.57 mmol) and TBTU (1.79 g, 5.57 mmol). The mixture stirred at room temperature for 4 hr, diluted with ethyl acetate, washed with saturated aq. NaHCO$_3$, saturated aq. NaCl, dried (Na$_2$SO$_4$), filtered and concentrated. The residue was purified by flash chromatography (67% ethyl acetate in hexane) to afford the sub-title compound as a colourless gum (1.05 g, 63%): $^1$H NMR (400 MHz, CDCl$_3$) δ 1.00-2.51 (6H, m), 3.05-3.38 (2H, m), 3.60-3.95 (3H, m), 4.35-4.95 (1H, m), 5.70-5.80 (1H, m), 7.55-7.95 (3H, m), 8.13-8.29 (1H, m), 8.48-8.61 (1H, m).

Method I: (S)-1-(Isoquinoline-1-carbonyl)-2-piperidinecarboxylic acid

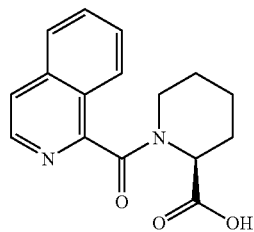

A stirred solution of (S)-1-(isoquinoline-1-carbonyl)-2-piperidinecarboxylic acid methyl ester (1.05 g, 3.52 mmol) in THF (20 ml) at room temperature was treated with water (10 ml). Lithium hydroxide (84 mg, 3.51 mmol) was then added and the resulting mixture was stirred at room temperature for 16 hrs. The resulting mixture was concentrated to remove the organic solvent. The resulting solution was then washed with diethyl ether and the remaining aqueous layer was made acid with 2 N HCl. The resulting solution was extracted with ethyl acetate and the organic layer was separated, dried (Na$_2$SO$_4$), filtered and concentrated to reveal a white solid (902 mg, 90%): $^1$H NMR (400 MHz, d$_4$-MeOH) δ 1.20-2.52 (6H, m), 3.10-3.39 (2H, m), 4.10-4.90 (1H, m), 7.68-8.55 (5H, m).

33

Method J: [3S/R,4S/R,(2S)]-5-Fluoro-4-hydroxy-3-[1-(isoquinoline-1-carbonyl)-2-piperidinecarboxamido]-pentanoic acid tert-butyl ester

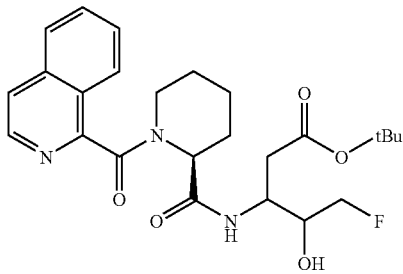

A stirred mixture of (S)-1-(isoquinoline-1-carbonyl)-2-piperidinecarboxylic acid (278 mg, 0.98 mmol), 3-amino-5-fluoro-4-hydroxy-pentanoic acid tert-butyl ester (213 mg, 1.03 mmol), HOBt (145 mg, 1.07 mmol), DMAP (137 mg, 1.12 mmol) and anhydrous THF (25 ml) was cooled to 0° C. then EDC (206 mg, 1.07 mmol) was added. The mixture was allowed to warm to room temperature during 16 hrs then concentrated under reduced pressure. The residue was purified by flash chromatography (5% methanol in DCM) to afford the title compound as a white foam (425 mg, 92%): $^1$H NMR (400 MHz, CDCl$_3$) δ 1.20-3.30 (17H, m), 3.95-4.18 (2H, m), 4.29-4.64 (4H, m), 4.86-5.01 (1H, m), 7.65-8.00 (4H, m), 8.10-9.00 (3H, m); $^{19}$F (376 MHz, CDCl$_3$) δ −229.39, −229.41, −229.57, −229.60, −229.64, −229.69, −230.41, −231.08.

[3S/R,(2S)]-5-Fluoro-4-oxo-3-[1-(isoquinoline-1-carbonyl)-2-piperidinecarboxamido]-pentanoic acid tert-butyl ester

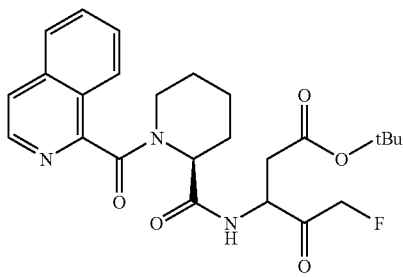

This sub-title compound was prepared using procedures similar to those described in method F as a white foam (268 mg, 63%): $^1$H NMR (400 MHz, CDCl$_3$) δ 1.20-2.60 (15H, m), 2.69-4.30 (4H, m), 4.83-5.78 (4H, m), 7.23-7.35 (1H, m), 7.57-8.00 (1H, m), 8.13-8.30 (1H, m), 8.45-8.72 (1H, m), 9.08-9.73 (1H, m); $^{19}$F (376 MHz, CDCl$_3$) δ −231.53, −231.69, −231.70, −232.13; MS (LR, ES) calculated for C$_{25}$H$_{30}$FN$_3$O$_5$: 471.5334, ES− 470.327, ES+ 472.270.

34

Method K: [3S/R,(2S)]-5-Fluoro-4-hydroxy-3-[1-(isoquinoline-1-carbonyl)-2-piperidinecarboxamido]-pentanoic acid trifluoroacetic acid salt

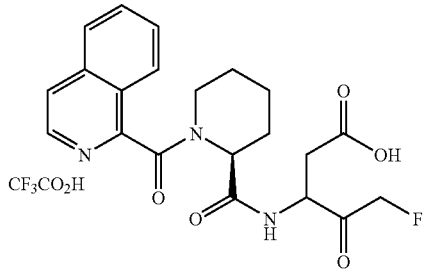

An ice cooled solution of trifluoroacetic acid (5 ml) in anhydrous DCM (5 ml) was added to a stirred ice cold solution of [3S/R,(2S)]-5-Fluoro-4-oxo-3-[1-(isoquinoline-1-carbonyl)-2-piperidine-carboxamido]-pentanoic acid tert-butyl ester (240 mg, 0.51 mmol) in anhydrous DCM (15 ml). The mixture was stirred at 0° C. for 2 hr and 4° C. for 40 hr. The mixture was concentrated under reduced pressure and the residue was dissolved in dry DCM. This process was repeated four times in order to remove excess trifluoroacetic acid. The gum was triturated with diethyl ether to afford the title compound as an off white solid (126 mg, 53%): IR (solid) 1794, 1736, 1646, 1441, 1250, 1198, 1150, 1055 cm$^{-1}$; $^1$H NMR (400 MHz, d$_6$-DMSO+TFA) δ 1.18-2.36 (6H, m), 2.59-3.45 (4H, m), 4.10-5.51 (4H, m), 7.60-8.78 (7H, m); $^{13}$C NMR (100 MHz, d$_6$-DMSO+TFA); $^{19}$F (376 MHz, d$_6$-DMSO) δ−226.75, −226.81, −227.00, −232.62, −232.66, −233.09; MS (LR, ES) calculated for C$_{21}$H$_{22}$FN$_3$O$_5$: 415.42, ES− 414.269, ES+ 416.198.

Example 3

[3S/R,(2S)]-5-Fluoro-4-oxo-3-[1-benzoyl-2-piperidinecarboxamido]-pentanoic acid (compound 3)

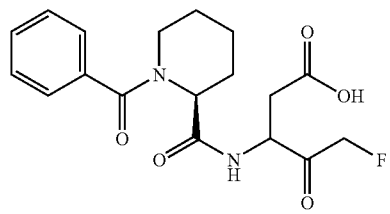

Method L: (S)-1-Benzoyl-2-piperidinecarboxylic acid methyl ester

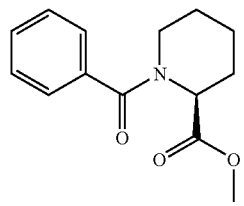

A stirred suspension of (S)-Piperidine-carboxylic acid methyl ester hydrochloride (1.009 g, 5.65 mmol) in anhydrous DCM (7 ml) at 0° C. was treated with diisopropylamine (3 ml, 17.34 mmol) and then benzoyl chloride (0.72 ml, 6.21 mmol). The resulting mixture was then stirred at 0° C. for 4 hr, before being diluted with DCM. The resulting solution was washed with 1 N HCl, saturated aq. NaHCO$_3$, saturated aq. NaCl, dried (MgSO$_4$), filtered and concentrated to reveal an oil. The residue was purified by flash chromatography (20% ethyl acetate in hexane) to afford the title compound as a colourless oil (1.221 g, 87%): $^1$H NMR (400 MHz, CDCl$_3$) δ 1.25-1.80 (5H, m), 2.10-2.39 (1H, m), 2.75-3.27 (1H, m), 3.55-3.68 (0.66H, m), 3.70-3.79 (3H, m), 5.41-5.54 (0.66H, m), 5.41-5.53 (0.66H, m), 7.26-7.46 (5H, m).

Method M: (S)-1-Benzoyl-2-piperidinecarboxylic acid

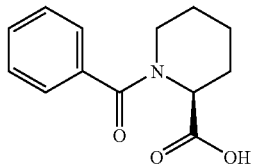

A stirred solution of (S)-1-benzoyl-2-piperidinecarboxylic acid methyl ester (1.221 g, 4.94 mmol) in a solution of methanol (5 ml) in water (5 ml) at 0° C. was treated with potassium hydroxide (305 mg, 5.43 mmol). The resulting mixture was stirred at 0° C. for 2 hr. A further quantity of potassium hydroxide (111 mg, 1.97 mmol) was then added and the resulting mixture was stirred for 1.5 hr, then concentrated. The resulting aqueous solution was then washed with DCM and the remaining aqueous layer was made acid with 1 N HCl. The resulting solution was extracted with ethyl acetate and the organics were separated, dried (MgSO$_4$), filtered and concentrated to reveal a crystalline solid (870 mg, 76%): $^1$H NMR (400 MHz, CDCl$_3$) 1.21-1.78 (5H, m), 1.98-2.27 (1H, m), 2.71-3.20 (1H, m), 3.28-3.38 (3H, m), 3.41-3.53 (0.5H, m), 4.21-4.47 (1H, m), 5.11-5.25 (0.5H, m), 7.27-7.39 (2H, m), 7.40-7.50 (3H, m).

The title compound was then prepared by subjecting (S)-1-Benzoyl-2-piperidinecarboxylic acid to procedures similar to those described in methods J, F and K. The product was isolated after RP-HPLC (MeCN/H$_2$O) as a white foam (25 mg, 10% last step): IR (solid) 3318, 2944, 1787, 1736, 1675, 1611 cm$^{-1}$; $^1$H NMR (400 MHz, d$_6$-DMSO) δ 1.37-1.63 (5H, m), 2.05-2.18 (1H, m) 2.60-2.94 (2H, m), 3.25-3.46 (2H, m), 4.34-4.77 (2H, m), 5.12-5.29 (2H, m), 7.34-7.90 (5H, m), 8.12-8.58 (1H, m); $^{13}$C NMR (100 MHz, d$_6$-DMSO) δ 20.54, 24.64, 25.11, 26.87, 27.80, 34.65, 45.82, 52.42, 58.46, 83.42, 126.37, 127.20, 128.74, 129.75, 129.86, 136.37, 171.38, 172.22, 173.33, 202.70, 202.82; $^{19}$F (376 MHz, d$_6$-DMSO) δ −226.52, −226.71, −226.84, −226.91, −230.13, −232.28, −232.39, −232.62, −232.66; MS (FAB+ve, HR) calculated for C$_{18}$H$_{21}$FN$_2$O$_5$ (MH+) 365.1513, found 365.1519.

Example 4

[3S/R,(2S)]-5-Fluoro-4-oxo-3-[1-(2-methyl-4-trifluoromethyl-thiazole-5-carbonyl)-2-piperidinecarboxamido]-pentanoic acid (Compound 4)

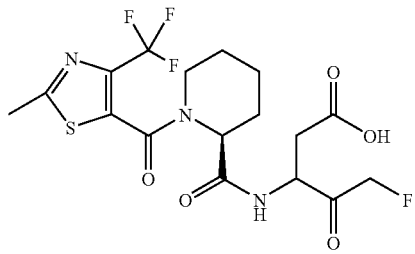

The title compound was prepared using procedures similar to those described in methods A-G. The product was isolated as a white foam (27.1 mg, 8% last step): IR (solid) 1794, 1736, 1632, 1436, 1355, 1203, 1165, 1126 cm$^{-1}$; $^1$H NMR (400 MHz, d$_6$-DMSO+TFA) δ 1.14-1.74 (6H, m), 2.01-2.23 (1H, m), 2.42-3.55 (7H, m), 4.06-4.80 (2H, m), 5.00-5.39 (2H, m), 8.02-8.71 (1H, m); $^{13}$C NMR (100 MHz, d$_6$-DMSO+TFA) δ 18.87, 19.07, 23.25, 23.85, 25.88, 31.47, 33.03, 33.20, 33.40, 44.18, 46.05, 46.16, 50.78, 50.82, 50.94, 51.02, 51.14, 51.26, 51.42, 56.58, 56.94, 80.08, 81.84, 81.93, 82.05, 83.73, 83.82, 102.44, 102.63, 116.52, 116.68, 116.90, 120.79, 122.31, 124.80, 125.55, 125.65, 129.02, 129.24, 129.32, 133.75, 135.65, 160.84, 161.00, 168.93, 169.18, 169.39, 170.64, 171.78, 172.64, 200.93, 201.26, 201.40; $^{19}$F (376 MHz, d$_6$-DMSO) δ −61.54, −226.61, −226.76, −226.86, −227.02, −228.01, −229.32, −229.86, −230.48, −231.39, −232.37, −232.55, −232.59, −232.69; MS (LR, ES) calculated for C$_{17}$H$_{19}$F$_4$N$_3$O$_5$S: 453.4157, ES− 452.327, ES+ 454.141.

Example 5

[3S/R,(2S)]-5-Fluoro-4-oxo-3-[1-(7-methoxy-benzofuran-2-carbonyl)-2-piperidine-carboxamido]-pentanoic acid (Compound 5)

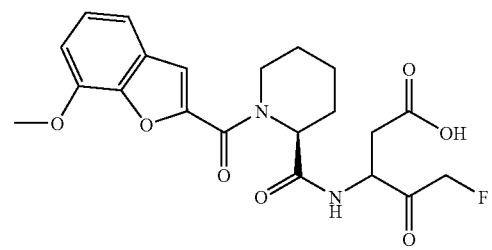

The title compound was prepared using procedures similar to those described in methods A-G. The product was isolated as a white foam (24.0 mg, 12% last step): IR (solid) 1794, 1736, 1627, 1589, 1427, 1269, 1203 cm$^{-1}$; $^1$H NMR (400 MHz, d$_6$-DMSO+TFA) δ 1.20-1.80 (4H, m), 2.10-2.29 (1H, m), 2.52-3.66 (5H, m), 4.05-5.42 (4H, m), 6.92-7.49 (4H, m), 8.29-8.90 (1H, m); $^{13}$C NMR (100 MHz, d$_6$-DMSO+TFA) δ 20.52, 20.75 24.64, 25.21, 27.00, 32.91, 34.61, 44.97 (CH$_2$), 47.73, 52.41, 52.66, 52.91, 53.25, 57.77 (CH, CH$_3$), 83.44, 85.21 (CH$_2$), 103.94, 104.13 (C), 108.71, 113.92, 124.78

(CH), 128.60, 143.56, 145.57, 148.54, 158.17, 158.55, 158.93, 159.32, 160.59, 160.78, 170.91, 172.21, 173.28, 202.66, 202.80; $^{19}$F (376 MHz, $d_6$-DMSO) δ −75.65, −226.85, −226.94, −228.09, −230.52, −230.83, −232.64, −232.74, −232.96; MS (LR, ES) calculated for $C_{21}H_{23}FN_2O_7$: 434.4251, ES− 433.386, ES+ 435.171.

Example 6

[3S/R,(2S)]-5-Fluoro-4-oxo-3-[1-(3-chloro-benzo[b] thiophene-2-carbonyl)-2-piperidinecarboxamido]-pentanoic acid (compound 6)

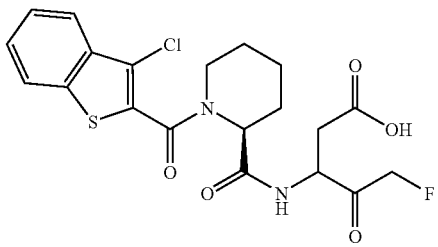

The title compound was prepared using procedures similar to those described in methods A-G. The product was isolated as a white foam (163 mg, 38% last step): IR (solid) 1803, 1736, 1674, 1622, 1527, 1417, 1269 cm$^{-1}$; $^1$H NMR (400 MHz, $d_6$-DMSO+TFA) δ 1.20-1.80 (6H, m), 2.00-2.30 (1H, m), 2.39-3.60 (3H, m), 4.20-4.82 (2H, m), 4.98-5.40 (2H, m), 7.42-7.69 (2H, m), 7.72-7.94 (1H, m), 7.99-8.20 (1H, m), 8.23-8.70 (1H m); $^{13}$C NMR (100 MHz, $d_6$-DMSO+TFA) δ 18.87, 19.07, 23.25, 23.85, 25.88, 31.47, 33.03, 33.20, 33.40, 44.18 ($CH_2$), 46.05, 46.16, 50.78, 50.82, 50.94, 51.02, 51.14, 51.26, 51.42, 56.58, 56.94 (CH), 80.08, 81.84, 81.93, 82.05, 83.73, 83.82 ($CH_2$), 102.44, 102.63, 116.52, 116.68, 116.90 (C), 120.79, 122.31, 124.80, 125.55, 125.65 (CH), 129.02, 129.24, 129.32, 133.75, 135.65, 160.84, 161.00, 168.93, 169.18, 169.39, 170.64, 171.78, 172.64, 200.93, 201.26, 201.40; $^{19}$F (376 MHz, $d_6$-DMSO+TFA) δ −226.55, −226.79, −226.87, −226.97, −229.76, −229.88, −230.67, −231.15, −232.35, −232.50, −232.56, −232.61; MS (LR, ES) calculated for $C_{20}H_{20}ClFN_2O_5S$: 454.9082, ES− 453.296, ES+ 455.12.

Example 7

[3S/R,(2S)]-5-Fluoro-4-oxo-3-[1-(3-chloro-thiophene-2-carbonyl)-2-piperidinecarboxamido]-pentanoic acid (Compound 7)

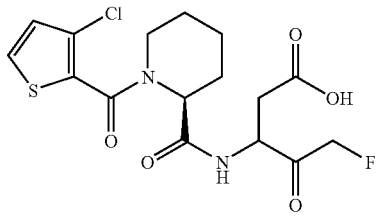

The title compound was prepared using procedures similar to those described in methods H-J, F and K. The product was isolated as a white foam: IR (solid) 1784, 1736, 1670, 1612, 1522, 1450, 1269 cm$^{-1}$; $^1$H NMR (400 MHz, CDCl$_3$) δ 1.13-1.80 (5H, m), 2.01-3.60 (5H, m), 4.11-5.36 (4H, m), 7.02-7.17 (1H, m), 7.70-7.90 (1H, m), 8.40-8.61 (1H, m); $^{19}$F (376 MHz, CDCl3) δ −226.90 (t), −232.65 (m); Low Res. MS (ES) calculated for $C_{16}H_{18}ClFN_2O_5S$: 404.8477, ES− 403.23, ES+ 405.062.

Example 8

[3S/R,(2S)]-5-Fluoro-4-oxo-3-[1-(benzofuran-2-carbonyl)-2-piperidinecarboxamido]pentanoic acid (Compound 8)

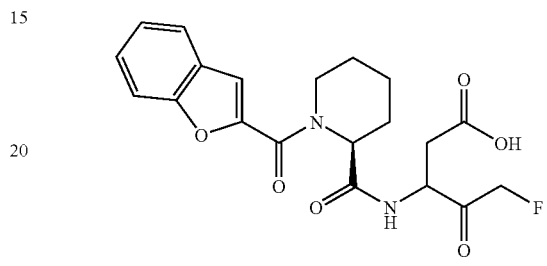

The title compound was prepared using procedures similar to those described in methods A-G. The product was isolated as a white foam (3.7 mg, 6% last step): $^1$H NMR (400 MHz, DMSO+TFA) δ 0.70-1.80 (5H, m), 2.10-3.60 (5H, m), 4.03-5.40 (4H, m), 7.20-7.83 (5H, m), 8.35-8.80 (1H, m); $^{19}$F (376 MHz, CDCl3) δ −226.75, −226.89, −232.71; Low Res. MS (ES) calculated for $C_{20}H_{21}CFN_2O_6$: 404.3986, ES− 403.359, ES+ 405.165.

Example 9

[3S/R,(2S)]-5-Fluoro-4-oxo-3-[1-[2-(3-trifluoromethyl-phenyl)-thiazole-4-carbonyl]-2-piperidinecarboxamido]-pentanoic acid (Compound 9)

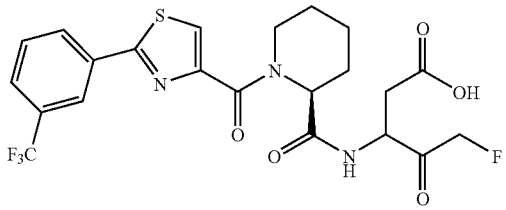

The title compound was prepared using procedures similar to those described in methods A-G. The product was isolated as a white foam (31 mg, 11% last step): IR (solid) 1789, 1741, 1617, 1512, 1441, 1417, 1327, 1231, 1169, 1122 cm$^{-1}$; $^1$H NMR (400 MHz, $d_6$-DMSO+TFA) δ 1.19-1.81 (5H, m), 2.04-3.55 (5H, m, Asp), 4.04-5.39 (4H, m), 7.64-8.36 (5H, m), 8.42-8.62 (1H, m); $^{13}$C NMR (100 MHz, $d_6$-DMSO+TFA) δ 20.54, 24.71, 25.13, 27.12, 27.88, 33.06, 34.54, 34.67, 45.29, 47.62, 52.28, 52.42, 53.09, 57.78, 83.22, 83.44, 85.22, 103.92, 104.11, 122.90, 125.50, 125.85, 127.35, 128.21, 129.95, 130.26, 130.58, 130.78, 131.07, 133.77, 151.09, 163.56, 163.97, 165.03, 171.12, 171.28, 172.10, 172.17, 202.81; $^{19}$F (376 MHz, $d_6$-DMSO) δ −61.76, −226.75, −226.85, −226.96, −227.04, −230.23, −230.35, −230.85, −232.49, −232.6, −232.64, −232.83; MS (LR, ES) calculated for $C_{22}H_{21}F_4N_3O_5S$: 515.4874, ES− 514.361, ES+ 516.167.

Example 10

[3S/R,(2S)]-5-Fluoro-4-oxo-3-[1-[2-(3-trifluoromethyl-phenyl)-furan-4-carbonyl]-2-piperidinecarboxamido]-pentanoic acid (Compound 10)

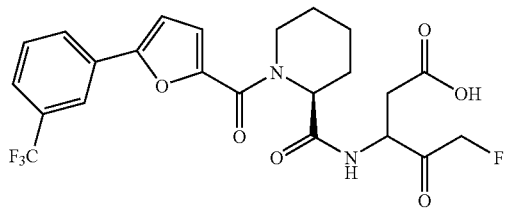

The title compound was prepared using procedures similar to those described in methods A-G. The product was isolated as a white foam (82 mg, 18% last step): IR (solid) 1794, 1736, 1670, 1603, 1522, 1431, 1331, 1255, 1165 cm$^{-1}$; $^1$H NMR (400 MHz, d$_6$-DMSO+TFA) δ 1.25-3.58 (10H, m), 4.18-5.34 (4H, m), 6.98-7.41 (2H, m), 7.62-7.78 (2H, m), 7.91-8.13 (2H, m), 8.10-8.80 (1H, m); $^{13}$C NMR (100 MHz, d$_6$-DMSO+TFA) δ 19.18, 19.42, 31.48, 33.13, 33.32, 50.87, 50.96, 81.95, 81.98, 83.73, 83.76, 102.49, 102.54, 102.69, 107.73, 116.84, 118.78, 119.28, 121.49, 123.66, 124.20, 126.62, 126.91, 128.68, 129.00, 129.16, 129.21, 129.31, 145.80, 145.87, 151.28, 151.39, 157.83, 158.40, 169.27, 169.64, 170.60, 170.70, 171.80, 201.16, 201.30, 201.43; $^{19}$F (376 MHz, d$_6$-DMSO+TFA) δ −61.63, −226.79, −232.56; MS (LR, ES) calculated for $C_{23}H_{22}F_4N_2O_6$: 498.4352, ES− 497.313, ES+ 499.233.

Example 11

[3S/R,(2S)]-5-Fluoro-3-{[1-(3-methyl-5-phenyl-thiophene-2-carbonyl) piperidine-2-carbonyl]-amino}-4-oxo-pentanoic acid (Compound 11)

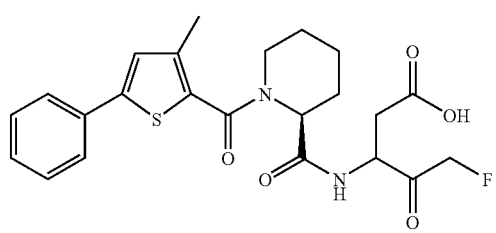

Method N:
5-Bromo-3-methyl-thiophene-2-carbaldehyde

A solution of 3-methylthiophene-2-carbaldehyde (10 g, 0.079 mol) in dichloromethane (10 ml) was added dropwise to a stirred solution of bromine (4.08 ml, 0.079 mol) in dichloromethane (15 ml) at room temperature. The resulting mixture was heated to reflux temperature for 3 hours before cooling to room temperature, washed with water (3×50 ml), saturated NaHCO$_3$ solution (2×25 ml), dried (MgSO$_4$) and the solvent removed at reduced pressure to give the sub-title compound as a brown solid (14.7 g, 66% yield): $^1$H NMR (400 MHz, CDCl3) δ$_H$ 2.60 (3H, s), 6.97 (1H, s) 9.20 (1H, s).

Method O:
3-Methyl-5-phenyl-thiophene-2-carbaldehyde

To a solution of 5-bromo-3-methyl-thiophene-2-carbaldehyde (1.00 g, 4.88 mmol) in ethylene glycol dimethyl ether (9 ml) was added phenylboronic acid (0.773 g, 6.34 mmol), 2M Na$_2$CO$_3$ solution (6.3 ml) and Pd(PPh$_3$)$_4$ (0.282 g, 0.24 mmol). The mixture was heated for 18 hours, cooled and the solvent removed at reduced pressure to leave a brown residue which was partitioned between water (15 ml) and dichloromethane (20 ml). The organic was separated, washed with water (2×5 ml), brine (10 ml), dried (MgSO$_4$) and the solvent removed at reduced pressure to give a brown oil. Purification by flash column chromatography (6:1 petrol 40-60° C./ethyl acetate) gave the sub-title compound as a yellow oil (0.90 g, 91% yield): $^1$H NMR (400 MHz, CDCl3) δ$_H$ 2.75 (3H, s), 7.25 (1H, s) 7.35-7.75 (5H, s), 10.05 (1H, s).

Method P:
3-Methyl-5-phenyl-thiophene-2-carboxylic acid

To a stirred solution of 3-methyl-5-phenyl-thiophene-2-carbaldehyde (0.200 g, 0.99 mmol) and 2-methyl-2-butene (2.77 g, 0.040 mol) in dimethylformamide (4 ml) at 0° C. was added NaClO$_2$ (0.894 g, 9.89 mmol) and NaH$_2$PO$_4$ (1.09 g, 7.91 mmol) in water (5 ml). The solution was allowed to warm to room temperature and stirred for 18 hours. The solvent was removed at reduced pressure and the residue partitioned between dichloromethane (10 ml) and 1N HCl solution (10 ml). The organic was separated, the aqueous layer extracted with dichloromethane (2×5 ml). The combined organic layers were dried (MgSO$_4$) and the solvent removed at reduced pressure to give a yellow oil. Purification by flash column chromatography 50% ethyl acetate/petrol 40-60° C.) gave the sub-title compound as a white solid (0.14 g, 69% yield): $^1$H NMR (400 MHz, CDCl3) δ$_H$ 2.65 (3H, s), 7.25 (1H, s) 7.35-7.80 (5H, s).

Method Q: [3S/R,(2S)]-5-Fluoro-3-{[1-(3-methyl-5-phenyl-thiophene-2-carbonyl) piperidine-2-carbonyl]-amino}-4-oxo-pentanoic acid The title compound was prepared from 3-methyl-5-phenyl-thiophene-2-carboxylic acid using procedures similar to those described in Methods F, H-K. The product was isolated as a white foam (0.066 g, 81% yield): IR (film) 1781.5, 1715.3, 1668.0, 1597.1, 1441.0, 1190.3 cm-1; $^1$H NMR (400 MHz, DMSO) δ$_H$ 1.00-1.80 (6H, m), 1.90-2.30 (4H, m), 2.70-3.90 (4H, m), 4.10-5.50 (4H, 2×m), 7.30-8.60 (6H, 4.∴m); $^{19}$F NMR (376 MHz, DMSO)−61.7, −224.3, −226.7, −226.8, −227.5, −232.7, −233.4; MS (FAB+ve, HR) Calculated for $C_{23}H_{24}FN_2O_5S$ (MH−) 459.52, found 459.40.

Example 12

[3S/R,(2S)]-5-Fluoro-3-({1-[3-methyl-5-(3-trifluoromethyl-phenyl)-thiophene-2-carbonyl]-piperidine-2-carbonyl}-amino)-4-oxo-pentanoic acid (Compound 12)

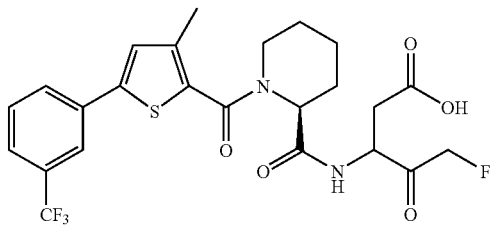

The title compound was prepared from 3-methylthiophene-2-carbaldehyde using procedures similar to those described in Methods F, H-K, N-P. The product was isolated as a pale pink solid (0.16 g, 94%): IR (film) 1784.0, 1726.9, 1664.9, 1588.7, 1436.2, 1326.6, 1164.6 cm-1; $^1$H NMR (400 MHz, DMSO) $\delta_H$ 1.00-1.80 (6H, m), 1.90-2.30 (4H, m), 2.70-4.05 (4H, m), 4.10-5.40 (4H, m), 7.00-9.00 (6H, m); $^{19}$F NMR (376 MHz, DMSO) −62.0, −224.3, −226.7, −226.9, −227.5, −232.6, −232.7, −233.4; MS (FAB+ve, HR) Calculated for $C_{24}H_{23}F_4N_2O_5S$ (MH−) 527.41, found 527.52.

Example 13

[3S/R,(2S)]-5-Fluoro-4-oxo-3-({1-[5-(3-trifluoromethyl-phenyl)-thiophene-2-carbonyl]-piperidine-2S-carbonyl}-amino)-pentanoic acid (Compound 13)

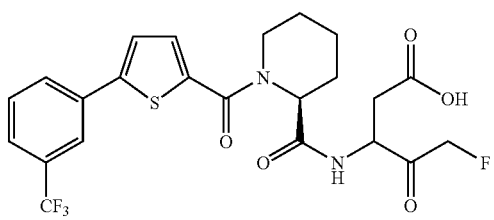

The title compound was prepared from thiophene-2-carbaldehyde using procedures similar to those described in Methods F, H-K, N-P. The product was isolated as a pale yellow solid (0.23 g, 93%): IR (film) 1784.0, 1722.1, 1664.9, 1588.7, 1531.5, 1321.8, 1164.6 cm-1; $^1$H NMR (400 MHz, DMSO) $\delta_H$ 0.90-1.85 (6H, m), 2.00-2.40 (1H, m), 2.45-3.50 (3H, m), 3.90-5.55 (4H, m), 7.00-9.05 (7H, m); $^{19}$F NMR (376 MHz, DMSO) −61.7, −224.3, −226.7, −226.8, −227.5, −227.6, −232.7, −233.4; MS (FAB+ve, HR) Calculated for $C_{23}H_{23}F_4N_2O_5S$ (MH+) 515.51, found 515.35.

Example 14

[3S/R,(2S)]-5-Fluoro-4-oxo-3-{[1-(pyridine-2-carbonyl)-piperidine-2-carbonyl]-amino}-pentanoic acid (Compound 14)

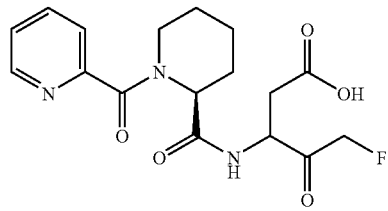

The title compound was prepared from pyridine-2-carboxylic acid using procedures similar to those described in Methods F, H-K. The product was isolated as a white solid (0.10 g, 93%): IR (film) 2945.4, 1650.5, 1446.6, 1186.5, 1139.9 cm$^{-1}$; $^1$H NMR (400 MHz, CDCl3) $\delta_H$ 1.40-1.80 (6H, m), 2.20-2.50 (1H, m), 2.69-3.12 (2H, m), 3.29-3.35 (1H, m), 3.48-3.51 (1H, m), 4.47-5.29 (3H, m), 7.37-9.11 (6H, m); $^{19}$F NMR (376 MHz, CDCl3) −231.69, −231.56, −231.44; MS (FAB+ve, HR) Calculated for $C_{17}H_{21}FN_3O_5$ (MH+) 366.36, found 366.4.

Example 15

[3S/R,(2S)]-3-{[1-(Biphenyl-3-carbonyl)-piperidine-2-carbonyl]-amino}-5-fluoro-4-oxo-pentanoic acid (Compound 15)

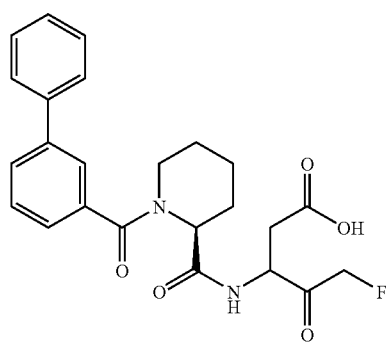

The title compound was prepared from 3-biphenylcarboxylic acid using procedures similar to those described in Methods F, H-K. The product was isolated as a white solid (0.13 g, 97%): IR (film) 2930.9, 1782.2, 1723.7, 1668.6, 1596.1, 1444.2, 1174.7 cm-1; $^1$H NMR (400 MHz, CDCl3) $\delta_H$ 1.40-1.90 (6H, m), 2.19-2.41 (1H, m), 2.70-3.30 (3H, m), 3.70-3.85 (1H, m), 4.30-5.50 (3H, m), 7.35-7.70 (11H, m); $^{19}$F NMR (376 MHz, CDCl3) −229.60, −229.88; MS (FAB+ve, HR) Calculated for $C_{24}H_{26}FN_2O_5$ (MH+) 441.46, found 441.4.

Biological Methods

Example 16

Enzyme Assays

The assays for caspase inhibition are based on the cleavage of a fluorogenic substrate by recombinant, purified human Caspases-1, -3, -7 or -8. The assays are run in essentially the same way as those reported in WO01/42216.

The compounds of examples 1-15 possess $K_{inact}$ values>5,000 $M^{-1}s^{-1}$ against caspases-1, -3 and -8.

Example 17

Inhibition of IL-1β secretion from Mixed Population of Peripheral Blood Mononuclear Cells (PBMC)

Processing of pre-IL-1β by caspase-1 can be measured in cell culture using a variety of cell sources. Human PBMC obtained from healthy donors provides a mixed population of lymphocyte and mononuclear cells that produce a spectrum of interleukins and cytokines in response to many classes of physiological stimulators. The assay conditions used for inhibition of IL-1β secretion from mixed population of peripheral blood mononuclear cells can be found in WO01/42216.

The inhibitory potency of the compounds can be represented by an $IC_{50}$ value, which is the concentration of inhibitor at which 50% of the mature IL-1β is detected in the supernatant as compared to the positive controls. Compound 10 of this invention showed an $IC_{50}$ of less than 0.5 µM in inhibition of IL-1β secretion from peripheral blood mononuclear cells as determined by the above methods.

Example 18

Anti-Fas Induced Apoptosis Assay

Cellular apoptosis can be induced by the binding of Fas ligand (FasL) to its receptor, CD95 (Fas). Conditions for an assay to measure the effect of compounds on the inhibition of the caspase-8-mediated apoptotic pathway can be found in WO01/42216.

Compound 3 of this invention showed an $IC_{50}$ of less than 0.05 µM in the FAS induced apoptosis assay.

Example 19

Inhibition of TNF Release from Whole Blood

Human blood was freshly drawn from healthy donors and collected in vacutainers. Blood was diluted 1:2 in PBS (tissue culture, pyrogen free) in a sterile bottle and inverted to mix well. Aliquots of 0.5 ml of blood mixture were dispensed into cluster tubes in 96 well format.

Dilutions of the test compounds were prepared in RPMI by taking 100 mM DMSO stocks of the compounds and diluting 1:10 in RPMI medium in eppendorfs, to give a 10 mM stock. 1:5 serial dilutions were prepared from the stock solutions.

LPS was kept at a frozen stock (−20 degrees C.) at 1 mg/ml in PBS and then diluted to 1:10 with RPMI medium and finally diluted in the medium again 1:350. 50 µl of each test compound (first concentration was 100 µM) were added to the blood samples and then stimulated with 10 µl LPS (final concentration in the well is 5 ng/ml). The contents were gently mixed using an 8 well multi-channel pipette and incubated at 37° C. over night. At the end of the incubation time, contents were gently mixed, then spun down at 1000×g for 5 mins at 20° C. The serum supernatants were transferred to a fresh plate without disturbing the RBCs and diluted 1:2 with the diluent RD6C.

TNF-alpha levels of supernatants were assayed using the R+D systems ELISA kit, using R+D systems protocol. Samples were read at 450 nm. Most preferred compounds of this invention showed $IC_{50}$ of less than 6 µM in the LPS-induced TNF-alpha assay in whole blood.

Compound 10 of this invention showed an $IC_{50}$ of less than 6 µM (5044 nM) in the LPS induced TNF-alpha assay in whole blood.

While we have described a number of embodiments of this invention, it is apparent that our basic examples can be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound of the formula I:

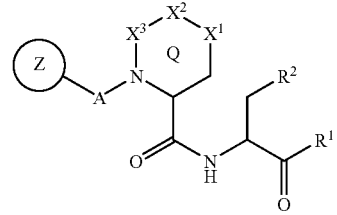

wherein:
$R^1$ is hydrogen, CN, CHN$_2$, R, or —CH$_2$Y;
R is an aliphatic group, a substituted aliphatic group, an aryl group, a substituted aryl group, an aralkyl group, a substituted aralkyl group, a non-aromatic heterocyclic group, or a substituted non-aromatic heterocyclic group;
Y is an electronegative leaving group, —OR, —SR, —OC═O(R), or —OPO($R^3$)($R^4$);
$R^3$ and $R^4$ are independently R or OR;
$R^2$ is CO$_2$H, CH$_2$CO$_2$H, or optionally substituted esters, amides or isosteres thereof;
A is C═O or SO$_2$;
$X^1$ is oxygen, sulfur, —NH, or —CH$_2$, wherein —NH is optionally substituted by an alkyl group, a cycloalkyl group, a (cycloalkyl)alkyl group, an amino acid N-terminal protecting group, or COR and —CH$_2$ is optionally substituted by fluorine, an alkyl group, a cycloalkyl group, a (cycloalkyl)alkyl group, an aralkyl group, an aryl group, an alkyloxy group, an alkylthioxy group, an aryloxy group, an arylthioxy group, an oxo group (i.e., ═O), or a NHCOR group;
$X^2$ is oxygen, sulfur, —NH, or —CH$_2$, wherein —NH is optionally substituted by an alkyl group, or an amino acid N-terminal protecting group and —CH$_2$ is optionally substituted by an alkyl group, an aryl group, an alkyloxy group, an alkylthioxy group, an aryloxy group, an arylthioxy group, or an oxo (i.e., ═O) group, a NHCOR group; $X^1$ and $X^2$ optionally form part of a phenyl ring that is fused to the adjoining ring Q;
$X^3$ is CH$_2$ or $X^2$ and $X^3$ optionally form part of a phenyl ring that is fused to the adjoining ring Q, provided that when $X^2$ forms a ring with $X^3$, then $X^2$ does not form a ring with $X^1$;

any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon;

or a pharmaceutically acceptable derivative thereof.

2. The compound of claim 1 wherein $R^1$ is $CH_2Y$ and Y is F, OR, SR, or —OC(=O)(R).

3. The compound of claim 2 wherein Y is F.

4. The compound of claim 2 wherein $R^2$ is $CO_2H$, an ester, amide, or carboxylic acid isostere.

5. The compound of claim 4 wherein $R^2$ is $CO_2H$.

6. The compound of claim 4 wherein $X^1$ and $X^2$ are each $CH_2$, or $X^1$ and $X^2$ combine to form part of an optionally substituted phenyl ring fused to ring Q.

7. The compound of claim 6 wherein $X^1$ and $X^2$ are each $CH_2$.

8. The compound of claim 7 wherein A is CO.

9. The compound of claim 8 wherein Z is an optionally substituted aryl which is connected to A at a ring carbon.

10. The compound of claim 1 selected from Table 1 below:

TABLE 1

Representative Compounds

| No. | Z |
|---|---|
| 1 | 4-methyl-2-phenylthiazole |
| 2 | 1-methylisoquinoline |
| 3 | methylbenzene (tolyl) |
| 4 | 2,5-dimethyl-4-(trifluoromethyl)thiazole |
| 5 | 7-methoxy-2-methylbenzofuran |

TABLE 1-continued

Representative Compounds

| No. | Z |
|---|---|
| 6 | 3-chloro-2-methylbenzothiophene |
| 7 | 3-chloro-2-methylthiophene |
| 8 | 2-methylbenzofuran |
| 9 | 4-methyl-2-[3-(trifluoromethyl)phenyl]thiazole |
| 10 | 5-methyl-2-[3-(trifluoromethyl)phenyl]furan |
| 11 | 3-methyl-4-phenyl-2-methylthiophene (Me, phenyl, Me on thiophene) |
| 12 | 3-methyl-2-methyl-5-[3-(trifluoromethyl)phenyl]thiophene |
| 13 | 5-methyl-2-[3-(trifluoromethyl)phenyl]thiophene |
| 14 | 2-methylpyridine |

TABLE 1-continued

Representative Compounds

| No. | Z (structure shown with piperidine-carbonyl-amide-CH₂F ketoacid scaffold) |
|---|---|
| 15 | 3-methylbiphenyl |
| 16 | 3,5-dichloro-2-methylbenzo[b]thiophene |
| 17 | 3,7-dichloro-2-methylbenzo[b]thiophene |
| 18 | 2-methyl-4-oxo-1H-quinoline |
| 19 | N-(p-tolyl)aminomethyl-1H-indole |
| 20 | 1-benzyl-3-methyl-1H-indole |

TABLE 1-continued

Representative Compounds

| No. | Z |
|---|---|
| 21 | 1-(3-methylbenzyl)-5-(trifluoromethyl)pyridin-2(1H)-one |
| 22 | 3-methylphenyl phenyl sulfoxide |
| 23 | 2-(benzylthio)-6-methylpyrazine |
| 24 | 3-methyl-benzylbenzene (1-benzyl-3-methylbenzene) |
| 25 | methylcyclohexane |

11. A pharmaceutical composition comprising: a) a compound or a pharmaceutically acceptable derivative thereof according to claim 1; and b) a pharmaceutically acceptable carrier, adjuvant or vehicle.

12. A kit comprising a caspase inhibitor and a tool for measuring TNF-alpha levels or activity.

* * * * *